(12) United States Patent
Takasugi et al.

(10) Patent No.: US 8,711,205 B2
(45) Date of Patent: Apr. 29, 2014

(54) IMAGE DISPLAY DEVICE AND CAPSULE ENDOSCOPE SYSTEM

(75) Inventors: Kei Takasugi, Hino (JP); Satomi Kobayashi, Kokubunji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/466,167

(22) Filed: May 8, 2012

(65) Prior Publication Data

US 2012/0274743 A1    Nov. 1, 2012

Related U.S. Application Data

(63) Continuation of application No. PCT/JP2011/074345, filed on Oct. 21, 2011.

(30) Foreign Application Priority Data

Nov. 8, 2010  (JP) ................................ 2010-250074

(51) Int. Cl.
*A61B 1/04* (2006.01)

(52) U.S. Cl.
USPC .......................................................... 348/45

(58) Field of Classification Search
USPC ................. 348/65, 45; 600/117, 424; 606/46; 382/128
See application file for complete search history.

(56) References Cited

U.S. PATENT DOCUMENTS

| | | | | |
|---|---|---|---|---|
| 5,463,698 A | * | 10/1995 | Meyer | 382/276 |
| 2002/0177779 A1 | * | 11/2002 | Adler et al. | 600/476 |
| 2006/0202998 A1 | * | 9/2006 | Hirakawa et al. | 345/501 |
| 2007/0292011 A1 | * | 12/2007 | Nishimura et al. | 382/128 |
| 2010/0016661 A1 | | 1/2010 | Nagase et al. | |

FOREIGN PATENT DOCUMENTS

| | | |
|---|---|---|
| EP | 1 618 828 A1 | 1/2006 |
| JP | 2005-168524 A | 6/2005 |
| JP | 2005-218584 A | 8/2005 |
| JP | 2006-75301 A | 3/2006 |
| JP | 2007-111205 A | 5/2007 |
| JP | 2007-283001 A | 11/2007 |
| JP | 2007-319478 A | 12/2007 |
| JP | 2008-301877 A | 12/2008 |

OTHER PUBLICATIONS

Mathematica documentation for MatrixPlot function published in Jul. 2000.*
International Search Report PCT/JP2011/074345 dated Jan. 17, 2012.
European Search Report dated May 24, 2013 from corresponding European Application No. 11 84 0277.5.

* cited by examiner

*Primary Examiner* — Mehrdad Dastouri
*Assistant Examiner* — Mohammed Rahaman
(74) *Attorney, Agent, or Firm* — Scully, Scott, Murphy & Presser, P.C.

(57) ABSTRACT

An image display device includes: a memory unit that stores internal body image data acquired via a receiver from a capsule endoscope taking internal body image of a subject and information that is associated with the internal body image data and related to a position of the capsule endoscope within the subject; a position information acquisition unit that performs a position estimation process based on the information related to the position to acquire position information of the capsule endoscope at imaging each of the internal body images; a preferential image determination unit that determines whether each of the internal body images meets a predetermined condition; and a preferential process control unit that controls the position information acquisition unit to perform the position estimation process preferentially on the internal body image determined to meet the predetermined condition by the preferential image determination unit.

8 Claims, 19 Drawing Sheets

IMAGE DISPLAY DEVICE AND CAPSULE ENDOSCOPE SYSTEM

CROSS REFERENCES TO RELATED APPLICATIONS

This application is a continuation of PCT international application Ser. No. PCT/JP2011/074345 filed on Oct. 21, 2011 which designates the United States, incorporated herein by reference, and which claims the benefit of priority from Japanese Patent Applications No. 2010-250074, filed on Nov. 8, 2010, incorporated herein by reference.

BACKGROUND OF THE INVENTION

1. Field of the Invention

The invention relates to an image display device that displays internal body images acquired by a capsule endoscope introduced in the body of a subject, and a capsule endoscope system.

2. Description of the Related Art

Conventionally, in performing a physical examination of a subject using a capsule endoscope introduced in the subject to image the inside of the subject, an internal body image group acquired by the capsule endoscope is observed in pseudo moving images or in the list of still images, and some of the images with abnormality are picked up. This work is called interpretation of radiogram.

If any abnormality is found by interpretation of radiogram, it is needed to identify what site (what organ) in the body of the subject is abnormal. Accordingly, there have been suggested some image display devices estimating the position of a capsule endoscope taking an internal body image (for example, refer to Japanese Laid-open Patent Publication No. 2006-75301, Japanese Laid-open Patent Publication No. 2007-283001, and Japanese Laid-open Patent Publication No. 2008-301877).

SUMMARY OF THE INVENTION

An image display device according to an aspect of the invention displays an internal body image group based on internal body image data acquired from a capsule endoscope taking internal body images of a subject, via a receiver conducting wireless communications with the capsule endoscope, the image display device including: a memory unit that stores the internal body image data and information associated with the internal body image data and related to a position of the capsule endoscope within the subject; a position information acquisition unit that performs a position estimation process based on the information related to the position to acquire position information of the capsule endoscope at imaging of each of the internal body images; a determination unit that determines whether each of the internal body images meets a predetermined condition; and a preferential process control unit that controls the position information acquisition unit to perform the position estimation process preferentially on the internal body image determined to meet the predetermined condition by the determination unit.

A capsule endoscope system according to another aspect of the invention includes: a capsule endoscope that is introduced in a body of a subject to take images and generate internal body image data representing internal body images of the subject; a receiver that receives the internal body image data generated by the capsule endoscope via wireless communication; and the image display device.

An image display device according to still another aspect of the invention displays an internal body image group based on internal body image data acquired from a capsule endoscope taking internal body images of a subject, the image display device including: a memory unit that stores the internal body image data and information associated with the internal body image data and related to a position of the capsule endoscope within the subject; a position information acquisition unit that performs a position estimation process based on the information related to a position to acquire position information of the capsule endoscope at imaging of each of the internal body images; a determination unit that determines whether results of predetermined image processing on the internal body image data meet a condition for performing a preferential process and provides a flag to the internal body image data meeting the condition; and a preferential process control unit that controls the position information acquisition unit to perform the position estimation process on the internal body image data provided with the flag by the determination unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An image display device and a capsule endoscope system according to one embodiment of the invention will be described below with reference to the drawings. In the following description, a system including a capsule endoscope introduced in the body of a subject and configured to take internal body images, is exemplified as an example, but the invention is not limited by this embodiment.

First Embodiment

Figure 1:
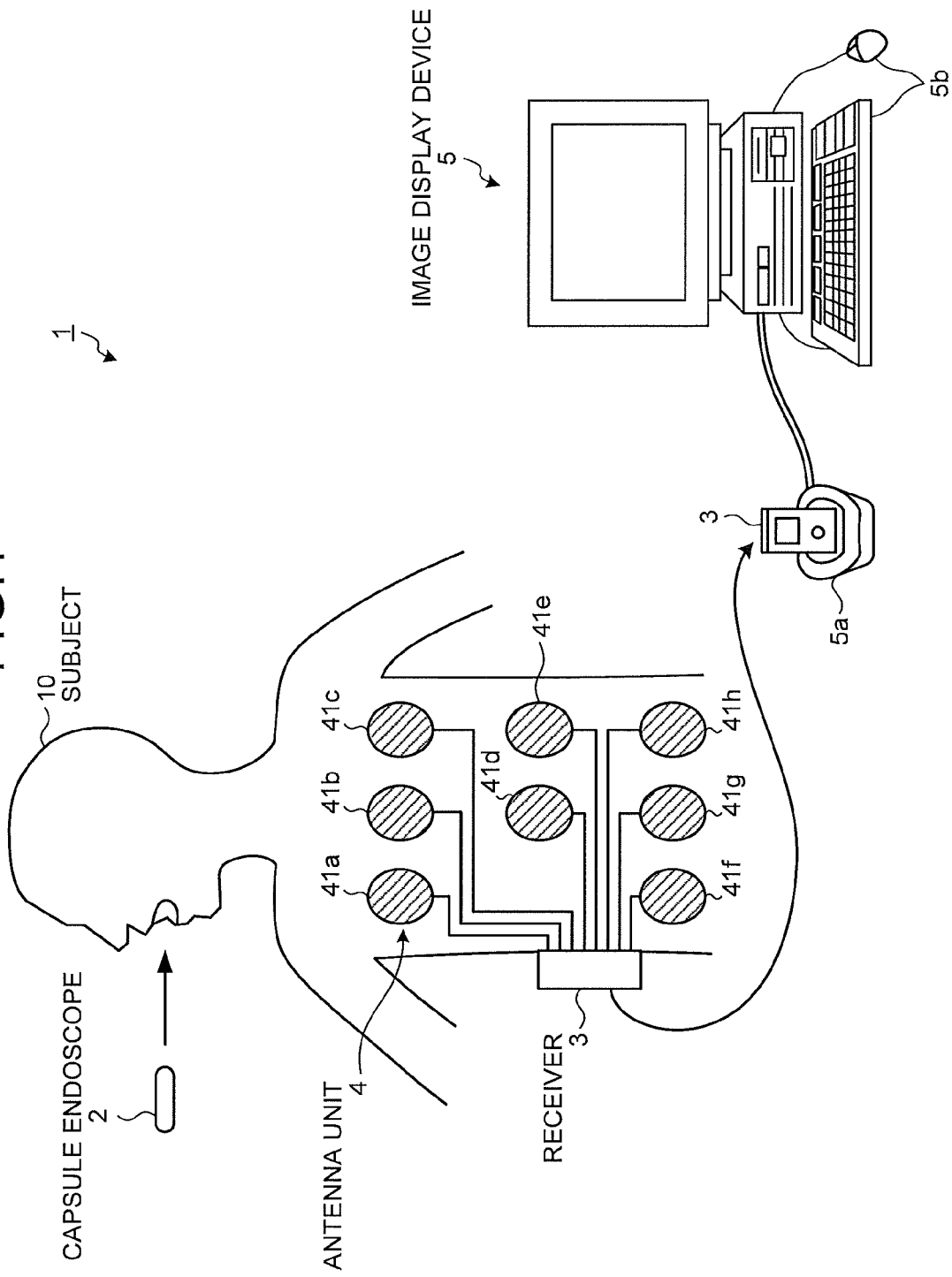
FIG. 1 is a schematic diagram illustrating an outline configuration of a capsule endoscope according to a first embodiment of the invention.

FIG. 1 is a schematic diagram illustrating an outline configuration of the capsule endoscope system according to a first embodiment of the invention. A capsule endoscope system 1 includes: a capsule endoscope 2 that is introduced in the body of a subject 10 to take images and transmit wirelessly image data of the internal body images to a receiver 3; the receiver 3 that receives the internal body image data wirelessly transmitted from the capsule endoscope 2; and an image display device 5 that displays internal body images based on the internal body image data received at the receiver 3.

The capsule endoscope 2 is swallowed by the mouth of the subject 10, and moves through organs of the subject 10 by peristalsis of the organs and the like while performing a predetermined signal process on image signals obtained by imaging the inside of the subject 10 in sequence at predetermined time intervals (for example, 0.5 second), thereby generating internal body image data. In addition, each time the capsule endoscope 2 takes an internal body image of the subject 10, the capsule endoscope 2 transmits wirelessly the generated internal body image data in sequence to the external receiver 3. The capsule endoscope 2 is assigned identification information (for example, a serial number) for identification of an individual capsule endoscope, and the identification information is also wirelessly transmitted together with the internal body image data.

The receiver 3 includes an antenna unit 4 having a plurality of reception antennas 41a to 41h. The reception antennas 41a to 41h are implemented using loop antennas, for example, and are placed at predetermined positions on an outer surface of the body of the subject 10 (positions corresponding to the organs in the body of the subject 10 through which the capsule endoscope 2 passes, for example). The positions of the reception antennas 41a to 41h may be changed arbitrarily depending on the purpose of examination, diagnosis, or the like. In addition, the number of antennas provided on the antenna unit 4 is not limited to eight corresponding to the reception antennas 41a to 41h, and may be smaller or larger than eight.

While the capsule endoscope 2 takes images (for example, a period of time between the instant when the capsule endoscope 2 is introduced in the subject 10 from the mouth and the instant when the capsule endoscope 2 is excreted through the digestive tract), the receiver 3 is carried by the subject 10 to receive internal body image data wirelessly transmitted from the capsule endoscope 2 via the antenna unit 4 and store the image data in a built-in memory. After completion of the imaging by the capsule endoscope 2, the receiver 3 is removed from the subject 10 and then is connected to the image display device 5 for transfer (downloading) of information such as internal body image data.

The image display device 5 is realized by a workstation, a personal computer, or the like including a display unit such as a CRT display or a liquid crystal display, and performs a predetermined process on internal body image data acquired via the receiver 3 and position-related information, and displays internal body images on the display unit. The image display device 5 is also connected to operation input devices 5b such as a keyboard and a mouse. Alternatively, the operation input device 5b may be a touch panel laid over the display unit. A user (interpreter) interprets internal body images of the subject 10 sequentially displayed on the image display device 5 while operating these operation input devices 5b, and observes (examinations) in-vivo sites in the body of the subject 10 (for example, esophagus, stomach, small intestine, large intestine, and the like), and performs a diagnosis on the subject 10 based on the result of the observation.

The image display device 5 includes an interface such as an USB (Universal Serial Bus) port. A cradle 5a is connected via the USB port to the image display device 5. The cradle 5a is a reading device reading internal body image data from a memory of the receiver 3. When the receiver 3 is attached to the cradle 5a, the receiver 3 is electrically connected to the image display device 5 to transfer internal body image data and its related information (reception strength information, time information, and identification information of the capsule endoscope 2) stored in the memory of the receiver 3, to the image display device 5. The image display device 5 thus acquires a series of internal body image data and its related information about the subject 10, and performs a process described later on the data to provide a screen of the internal body images. The image display device 5 may be connected to an output device such as a printer so as to output hard copies of the internal body images.

Figure 2:
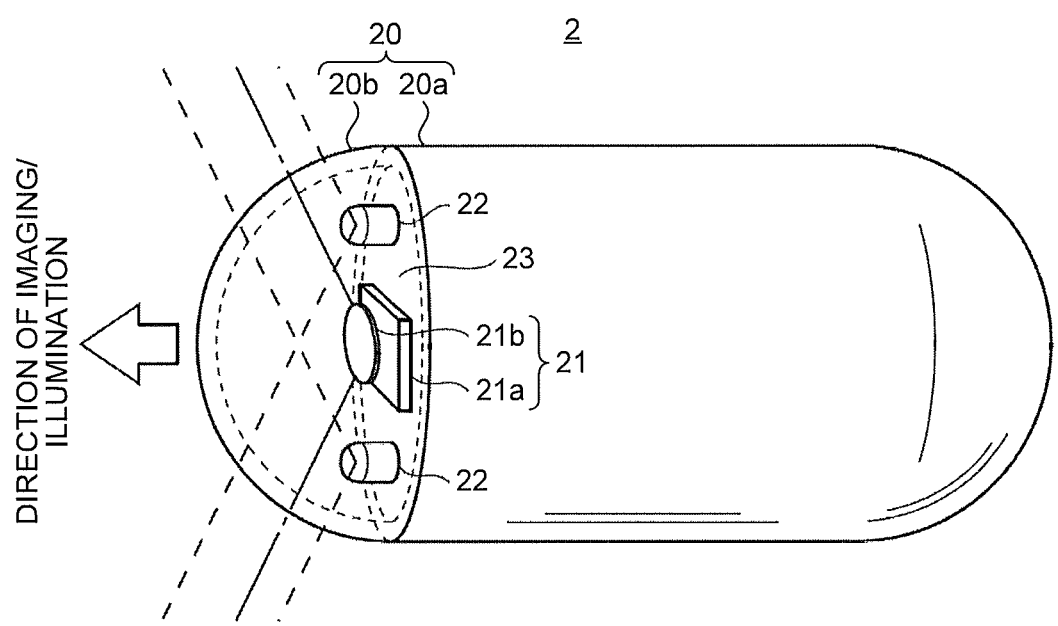
FIG. 2 is a schematic diagram illustrating an outline configuration of the capsule endoscope illustrated in FIG. 1.
Figure 3:
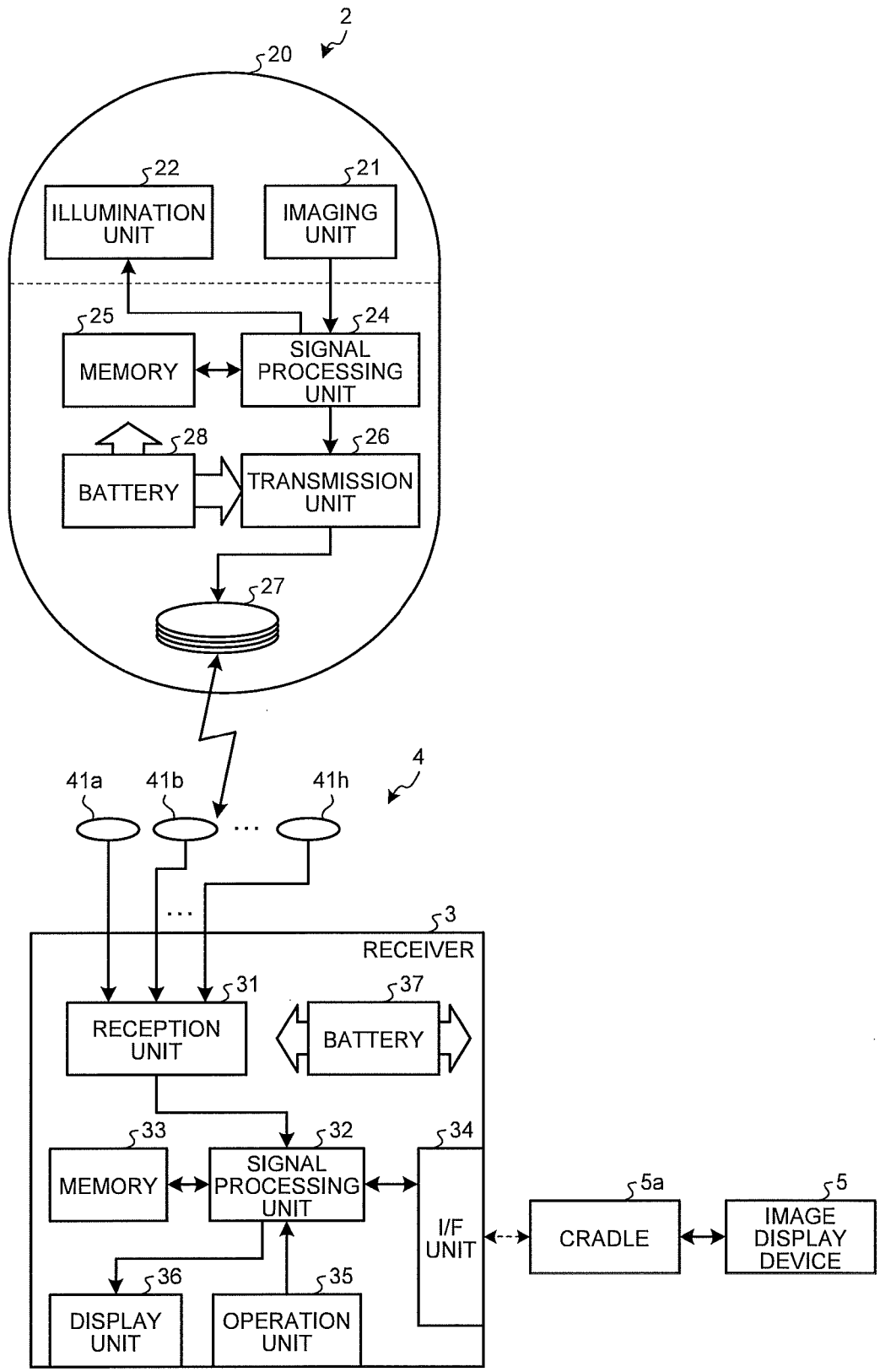
FIG. 3 is a block diagram illustrating a configuration of the capsule endoscope and a receiver illustrated in FIG. 1.

Next, components constituting the capsule endoscope system 1 will be described in detail. FIG. 2 is a schematic diagram illustrating one configuration example of the capsule endoscope 2. FIG. 3 is a block diagram illustrating a configuration of the capsule endoscope 2 and the receiver 3.

As illustrated in FIG. 2, the capsule endoscope 2 includes a capsule container 20 formed by an accommodating unit 20a and a hemispherical optical dome 20b. The capsule container 20 is sized so as to be configured to be swallowed by the subject 10, for example. The accommodating unit 20a has one end formed in the shape of a hemispherical dome and the other end opened and formed in the shape of an approximately cylinder. When the optical dome 20b is fitted to the accommodating unit 20a so as to cover the opening of the accommodating unit 20a, the inside of the capsule container 20 is sealed in a water-tight manner. In this embodiment, at least the optical dome 20b is made of a transparent material.

As illustrated in FIGS. 2 and 3, the capsule container 20 contains an imaging unit 21; an illumination unit 22; a circuit board 23 on which drive circuits and the like are provided to drive the imaging unit 21 and the illumination unit 22; a signal processing unit 24; a memory 25; a transmission unit 26; an antenna 27; and a battery 28.

The imaging unit 21 includes: an imaging element 21a such as a CCD or a CMOS generating image data of internal body images of a subject from optical images formed on a light-receiving surface thereof; and an optical system 21b such as an object lens disposed on the light-receiving surface of the imaging element 21a. The illumination unit 22 is implemented by LEDs (Light Emitting Diodes) or the like. The imaging element 21a, the optical system 21b, and the illumination unit 22 are mounted on the circuit board 23.

The drive circuit for the imaging unit 21 operates under control of the signal processing unit 24 described later, and generates an image signal indicative of internal body images of the subject 10 on a periodic basis (for example, two frames per second), and inputs the image signal to the signal processing unit 24. The following description is based on the assumption that the imaging unit 21 and the illumination unit 22 each include their respective drive circuits.

The circuit board 23 on which imaging unit 21 and the illumination unit 22 are mounted are attached to the opening of the accommodating unit 20a, such that the light receiving surface of the imaging element 21a and a direction of light radiation of the illumination unit 22 face toward the optical dome 20b. Therefore, a direction of imaging of the imaging unit 21 and a direction of illumination of the illumination unit 22 face toward the outside of the capsule endoscope 2 via the optical dome 20b as illustrated in FIG. 2. This makes it possible to image the inside of the subject 10 by the imaging unit 21 while illuminating the inside of the subject 10 by the illumination unit 22.

The signal processing unit 24 controls operations of individual units of the capsule endoscope 2, and subjects an image signal output from the imaging unit 21 to A/D conversion to generate digital internal body image data, and further performs a predetermined signal process on the digital data. The memory 25 stores temporarily various operations to be performed by the signal processing unit 24 and internal body image data subjected to the signal process by the signal processing unit 24. The transmission unit 26 superimposes on a radio signal the internal body image data stored in the memory 25 together with the identification information of the capsule endoscope 2, and transmits the image data outward via the antenna 27. The battery 28 supplies power to the individual units of the capsule endoscope 2. The battery 28 includes a power source circuit raising power supplied from a primary battery or a secondary battery such as a button battery.

Meanwhile, the receiver 3 includes a reception unit 31, a signal processing unit 32, a memory 33, an interface (I/F) unit 34, an operation unit 35, a display unit 36, and a battery 37. The reception unit 31 receives the internal body image data transmitted wirelessly from the capsule endoscope 2 via the reception antennas 41a to 41h. The signal processing unit 32 controls operations of the individual units of the receiver 3, and performs a predetermined signal process on the internal body image data received at the reception unit 31. The memory 33 stores various operations to be performed by the signal processing unit 32, and internal body image data and its related information (reception strength information, time information, and the like) subjected to a signal process by the signal processing unit 32. The interface unit 34 transmits the internal body image data and its related information stored in the memory 33 to the image display device 5 via the cradle 5a. The operation unit 35 is intended for a user to input various operational instructions and settings to the receiver 3. The display unit 36 provides or displays various kinds of information to a user. The battery 37 supplies power to the individual units of the receiver 3.

The internal body image data received at the receiver 3 can be transferred to the image display device 5 in various manners other than the one described above. For example, the receiver 3 may use a memory detachable from the receiver 3 such as a USB memory or a compact flash (registered trademark). In this case, after internal body image data from the capsule endoscope 2 is stored in the memory, only the memory can be removed from the receiver 3 and inserted to a USB port or the like of the image display device 5, for example. Alternatively, the image display device 5 may be provided with a function of communicating with an external device so as to transmit the internal body image data from the receiver 3 to the image display device via wired or wireless communications.

Figure 4:
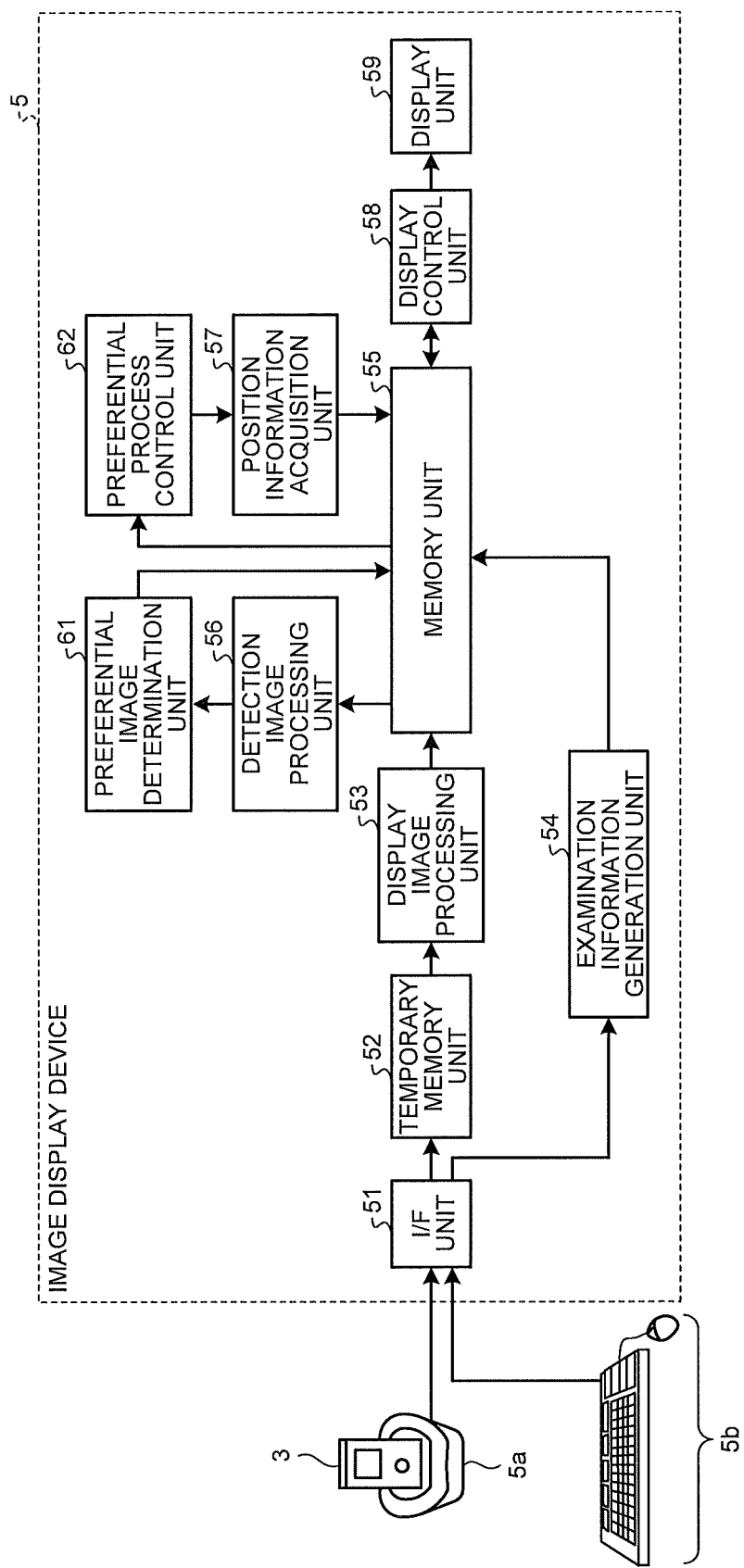
FIG. 4 is a block diagram illustrating a configuration of an image display device according to the first embodiment of the invention.

Next, the configuration of the image display device 5 illustrated in FIG. 1 will be described. FIG. 4 is a block diagram illustrating the configuration of the image display device 5. As illustrated in FIG. 4, the image display device 5 includes an interface (I/F) unit 51, a temporary memory unit 52, a display image processing unit 53, an examination information generation unit 54, a memory unit 55, a detection image processing unit 56, a position information acquisition unit 57, a display control unit 58, a display unit 59, a preferential image determination unit 61, and a preferential process control unit 62.

The interface unit 51 receives internal body image data and its related information input via the cradle 5a, and signals indicative of various instructions and information input via the operation input device 5b.

The temporary memory unit 52 is implemented by a volatile memory such as a DRAM or an SRAM, and temporarily stores the internal body image data and its related information input via the interface unit 51. Alternatively, instead of the temporary memory unit 52, a recording medium such as an HDD, an MO, a CD-R, and a DVD-R and a drive device driving the recording medium may be provided so that the internal body image data input from the interface unit 51 may be temporarily stored in the recording medium.

The display image processing unit 53 performs various kinds of display image processing for displaying internal body images on the display unit 59, on the internal body image data stored in the temporary memory unit 52, such as white balance processing, de-mosaicing, color conversion, concentration conversion (gamma conversion and the like), smoothing (denoising and the like), and sharpening (edge reinforcement and the like).

The examination information generation unit 54 generates information related to the examination based on the information input via the operation input device 5b. Specifically, the information includes patient information for identification of the subject 10 as a patient (ID, name, sex, age, date of birth, and the like), examination information for identification of examination of the subject 10 (the name of a hospital, the name of a doctor (nurse) in charge of capsule administration, the date and time of the capsule administration, the date and time of data acquisition, the serial number of the capsule endoscope 2, the serial number of the receiver 3, and the like). The examination information may be produced before or after transfer of the internal body image data from the receiver 3.

The memory unit 55 stores various process programs performed at the image display device 5, the internal body image data supplied to image processing by the display image processing unit 53, the examination information produced by the examination information generation unit 54, detection image information generated by the detection image processing unit 56 described later, position information acquired by the position information acquisition unit 57, and the like. The memory unit 55 is implemented by a flash memory, a semiconductor memory such as a RAM or a ROM, a recording medium such as an HDD, an MO, a CD-R, or a DVD-R, a drive device driving the recording medium, and the like.

The detection image processing unit 56 performs a detection image processing for detecting a site of lesion or a boundary between organs from the internal body images subjected to the display image processing. Specifically, the detection image processing includes an image recognition process for detecting a site of neoplastic, mucosal, or vascular lesion or the like, or a characteristic image area of a site of lesion related to bleeding, or an average color calculation process for identification of an organ or detection of a bleeding site.

The position information acquisition unit 57 performs a position estimation process based on the reception strength information and time information stored in the temporary memory unit 52, thereby to acquire information indicative of positional coordinates of the capsule endoscope 2 (position information) at taking each internal body image. Specifically, the position information acquisition unit 57 acquires reception strengths of the reception antennas 41*a* to 41*h* associated with the received internal body image data from the temporary memory unit 52, and extracts hemispheric areas with radii of distances according to the reception strengths, centered on the reception antennas 41*a* to 41*h*. The weaker the reception strengths become, the larger the radii become. A point at which these areas intersect with one another is estimated as the position of the capsule endoscope 2 at that time, that is, the position of the subject 10 imaged in the internal body image. The position information acquisition unit 57 causes the memory unit 55 to store the acquired position information in association with the corresponding internal body image data.

The display control unit 58 controls the display unit 59 to display the internal body images, their position information, and other various kinds of information in a predetermined form.

The display unit 59 is implemented by a CRT display or a liquid crystal display, and displays a radiogram interpretation screen on which the internal body images of the subject 10 are sequentially displayed, various kinds of information, and notification messages to a user, and the like, under control of the display control unit 58.

The preferential image determination unit 61 determines internal body images to be preferentially subjected to the position estimation process (hereinafter, referred to as "preferential images"), based on results of the detection image processing. In the first embodiment, internal body images in which a site of neoplastic, mucosal, or vascular lesion or a site of lesion related to bleeding is detected or a boundary between organs is imaged, are determined as preferential images. The preferential image determination unit 61 determines whether a site of lesion or a boundary between organs is extracted from the internal body images subjected to the detection image processing, and provides a flag indicative of preferential images to the internal body image data from which a site of lesion or a boundary between organs is extracted.

The preferential process control unit 62 controls the position information acquisition unit 57 to perform the position estimation process preferentially on the internal body image data determined as preferential images by the preferential image determination unit 61 (that is, the internal body image data provided with the flag).

Next, an operation of the image display device 5 will be described with reference to FIGS. 4 to 6. As illustrated in FIG. 4, when the receiver 3 is attached to the cradle 5*a*, the internal body image data and its related information stored in the memory of the receiver 3 are transferred to the image display device 5. The transferred internal body image data and the like are stored in the temporary memory unit 52. Upon completion of transfer of all of the internal body image data and its related information, the image display device 5 starts a data process on the data stored in the temporary memory unit 52.

Figure 5:
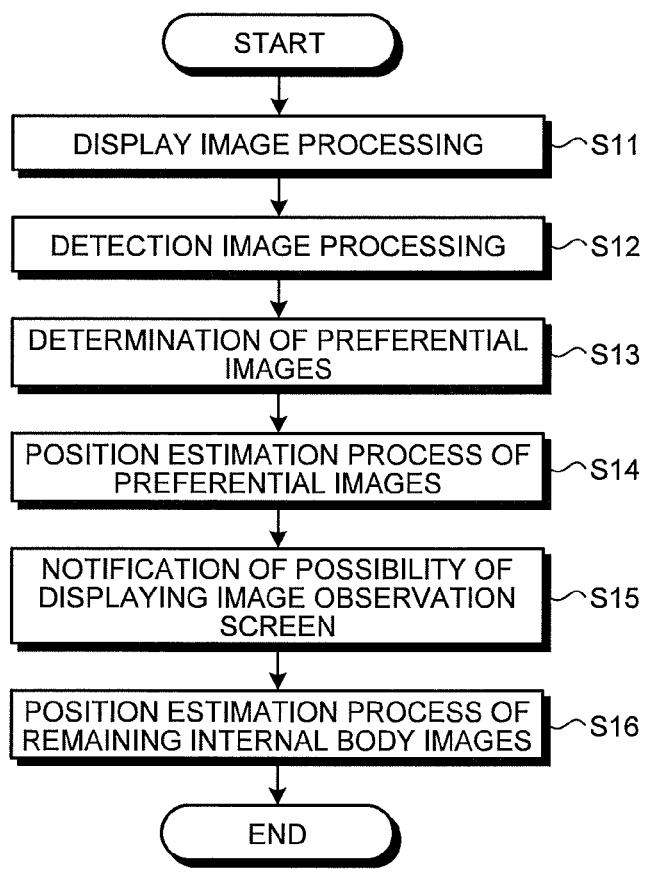
FIG. 5 is a flowchart showing an operation of the image display device illustrated in FIG. 4.

FIG. 5 is a flowchart showing an operation of the image display device 5.

First, at step S11, the display image processing unit 53 performs a display image processing on the internal body image data stored in the temporary memory unit 52. The internal body image data subjected to the display image processing is stored in the memory unit 55.

At step S12, the detection image processing unit 56 retrieves the internal body image data stored in the memory unit 55 in a sequential manner (for example, in order of transfer of the image data), and performs the detection image processing on the retrieved data. If a site of lesion or a boundary between organs or the like is detected from the internal body images, detected image information is generated. The detected image information is stored in the memory unit 55 in association with the internal body image data.

At subsequent step S13, the preferential image determination unit 61 provides a flag indicative of preferential images to the internal body image data in which a site of lesion or a boundary between organs or the like is detected by the detection image processing unit 56 (that is, the internal body image data having the detected image information).

At step S14, the position information acquisition unit 57 retrieves sequentially related information of the internal body image data provided with the flag indicative of preferential images from the memory unit 55, and performs the position estimation process on the retrieved information, under control of the preferential process control unit 62. Accordingly, the generated position information is stored in the memory unit 55 together with the reception time in association with the internal body image data.

At the image display device 5, upon completion of the position estimation process on the preferential images, it is possible to display the internal body images and minimum required position information on the display unit 59. Accordingly, at step S15, the display control unit 58 causes the display unit 59 to display a message informing a radiogram interpretation screen can be displayed. At that time, the display control unit 58 may cause the display unit 59 to display the radiogram interpretation screen after lapse of a predetermined time after displaying the message, or a screen that allows a user to select whether the radiogram interpretation screen is to be displayed or not with the message. In the latter case, the display control unit 58 causes the display unit 59 to display the radiogram interpretation screen when a signal indicative of selection of display of the radiogram interpretation screen is input by the user's operation.

At step S16, the position information acquisition unit 57 retrieves related information of the internal body image data other than the preferential images in a sequential manner (for example, in order of transfer of the image data), and performs the position estimation process on the retrieved information. Upon completion of the position estimation process on all of the internal body images, the data processing at the image display device 5 is terminated.

Figure 6:
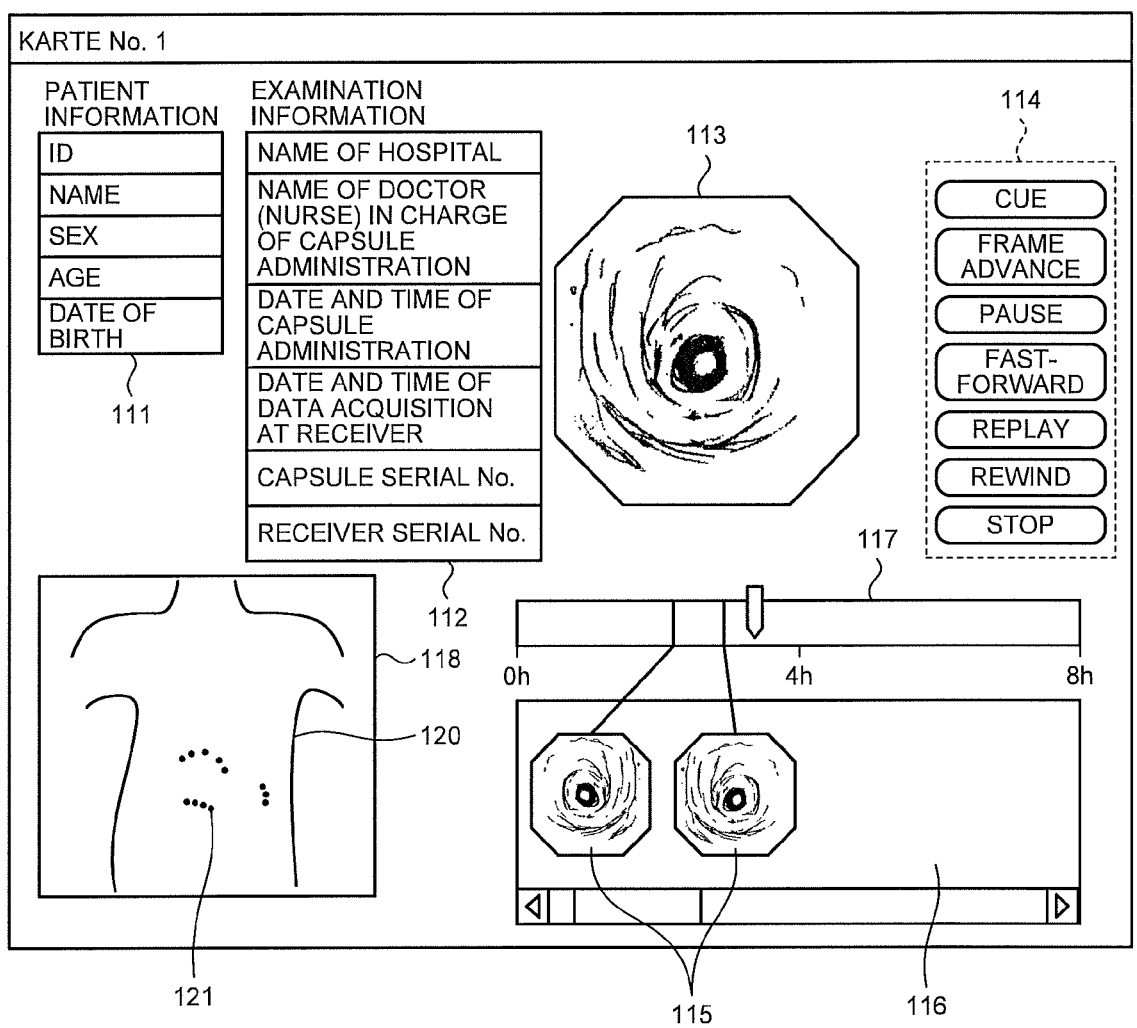
FIG. 6 is a schematic diagram illustrating a first display example of a radiogram interpretation screen.

FIG. 6 is a schematic diagram illustrating a display example of a radiogram interpretation screen displayed on the display unit 59 after step S15. After completion of the position estimation process on the preferential images, the display control unit 58 produces a radiogram interpretation screen 110 as illustrated in FIG. 6, for example, and causes the display unit 59 to display the radiogram interpretation screen 110.

The radiogram interpretation screen 110 includes: a patient information area 111 showing identification information of the subject 10 as a patient; an examination information area 112 showing identification information of an examination performed on the subject 10; a main display area 113 where a series of internal body images is reproduced; a reproduction operation button group 114 receiving input of an operation for reproduction of the internal body images displayed in the main display area 113; a thumbnail area 116 where minified images 115 of a plurality of internal body images are displayed in thumbnailed form; a time bar 117 indicating the time when the internal body images currently displayed in the main display area 113 were acquired; and a position display area 118 where imaging positions of the internal body images are shown. In the radiogram interpretation screen 110, the minified images 115 and points on the time bar 117 indicating the times when the minified images 115 were acquired, are linked by lines.

In the position display area 118, a personal image 120 representing the subject 10 is displayed. The imaging positions of the internal body images are represented by points 121 on the personal image 120, based on the position information acquired by the position information acquisition unit 57. When a signal to select any of the points 121 is input into the image display device 5 by a user's pointer operation or the like, the display control unit 58 may control the display unit 59 to display the internal body image corresponding to the selected point 121 in the main display area 113.

When the position estimation process on the preferential images is completed, there exists only the position information of the preferential images, and thus only the imaging positions of the preferential images (that is, internal body images containing a site of lesion or a boundary between organs) are shown in the position display area 118. After that, when the position estimation process is performed on the internal body images other than the preferential images, an increasing number of the points 121 are shown in the position display area 118. In this arrangement, the points 121 corresponding to the preferential images and the points 121 corresponding to the internal body images other than the preferential images may be shown by different colors, marks, or brightnesses, for example, so that the points 121 can be differentiated.

Figure 7:
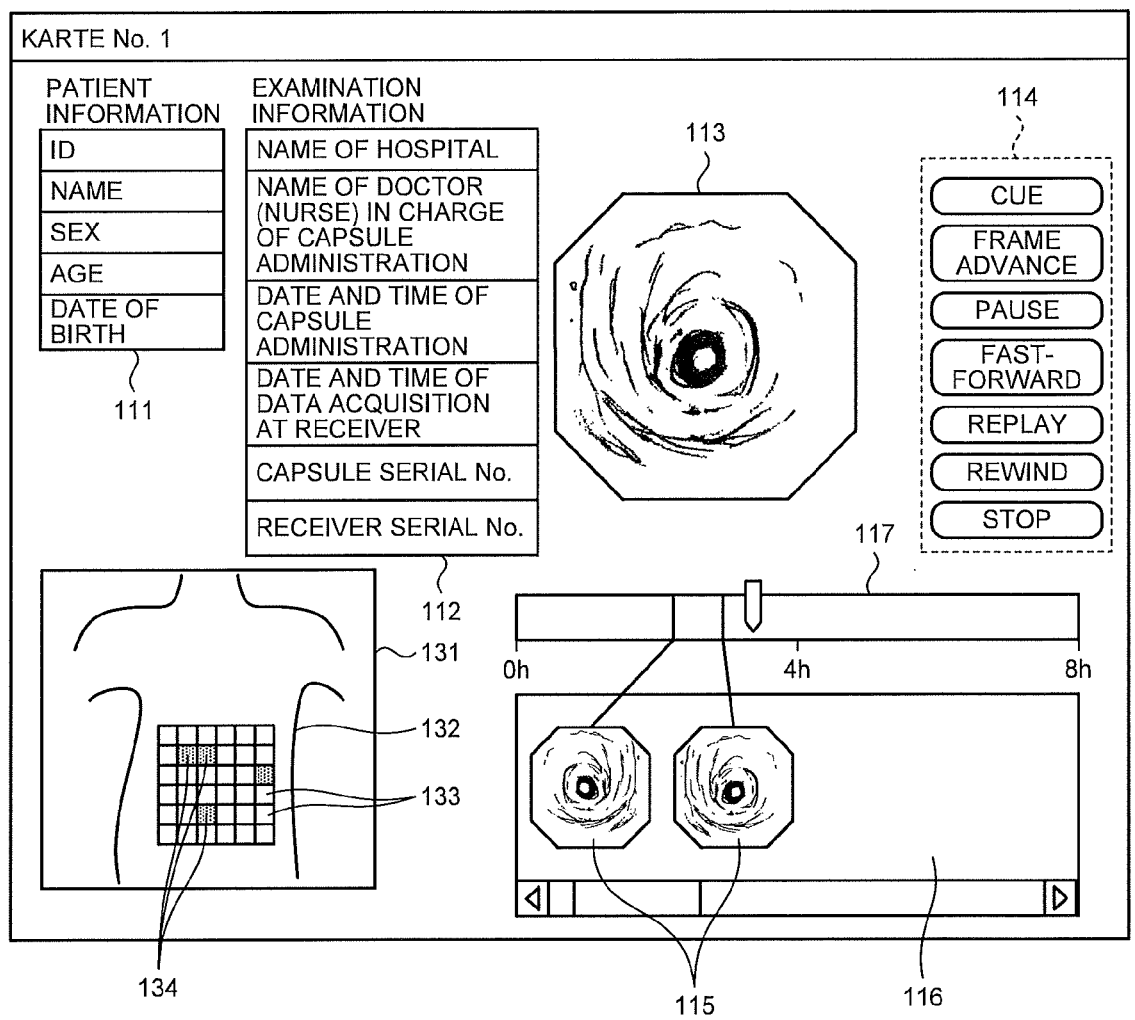
FIG. 7 is a schematic diagram illustrating a second display example of a radiogram interpretation screen.

FIG. 7 is a schematic diagram illustrating another display example of a radiogram interpretation screen on the display unit 59. A radiogram interpretation screen 130 illustrated in FIG. 7 includes a position display area 131 instead of the position display area 118 of FIG. 6. The position display area 131 shows a personal image 132 representing the subject 10 and a plurality of sub-areas (divided areas) 133 divided in a 6×6 matrix, for example. The imaging positions of the internal body images are expressed by filling corresponding divided areas 133 on the personal image 132 with a predetermined color or pattern based on the position information acquired by the position information acquisition unit 57. FIG. 7 illustrates a plurality of filled divided areas 134. Color and brightness of the divided areas 134 may be changed depending on the number of the internal body images including the divided areas 134 as imaging positions. Specifically, the brightness of the divided areas dense with the imaging positions may be increased. In addition, when a signal to select any of the divided areas 134 is input into the image display device 5 by a user's pointer operation or the like, the internal body image corresponding to the divided area may be shown in the main display area 113.

After completion of the position estimation process on the preferential images, the display control unit 58 may provide the divided areas 133 in a sub-divided manner (for example, in a 9×9 matrix or the like), according to the progress of the position estimation process on the internal body images other than the preferential images.

As described above, according to the first embodiment, the position estimation process is preferentially performed on the internal body images in which a site of lesion or a boundary between organs is detected by the detection image processing, and the radiogram interpretation screen is displayed upon completion of the preferential position estimation process, and therefore, the user can start early radiogram interpretation without waiting for the completion of the position estimation process on all of the internal body images. In addition, at the beginning of radiogram interpretation, the position information of the important internal body images to be noted at examination has already acquired, and thus the user can early grasp the imaging positions of the internal body images and efficiently perform interpretation of radiogram.

In the foregoing description, after completion of the display image processing on all of the internal body images, the detection image processing unit 56 starts the detection image processing. Alternatively, after the internal body image data subjected to the display image processing starts to be stored in the memory unit 55, the detection image processing unit 56 may perform the detection image processing in parallel with the display image processing.

In the foregoing description, after completion of the detection image processing on all of the internal body images, the position information acquisition unit 57 starts the position estimation process on the preferential images. Alternatively, the position information acquisition unit 57 may perform the position estimation process in parallel with the start of the detection image processing. In this case, the preferential process control unit 62 controls the position information acquisition unit 57 to, at generation of any preferential image, interpose the preferential image to the detection image processing and perform a position estimation process on the preferential image.

Second Embodiment

Figure 8:
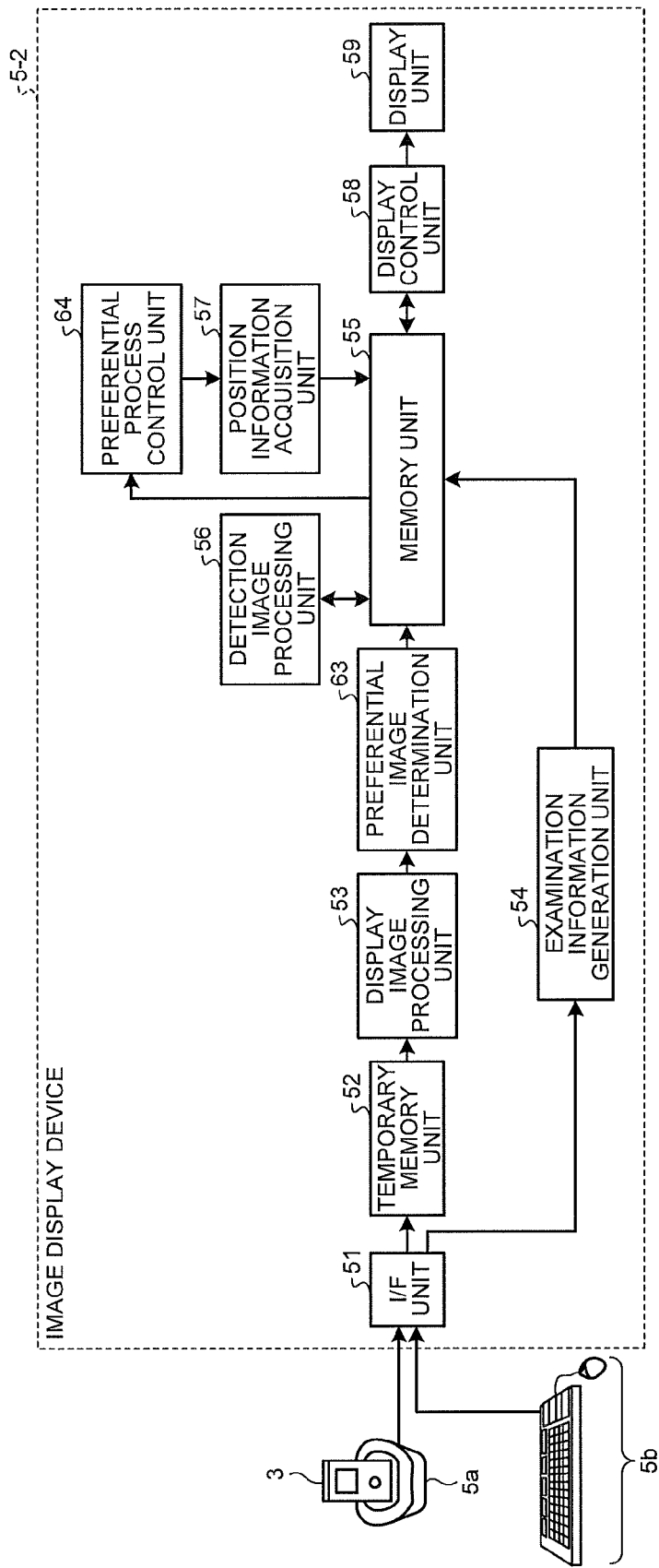
FIG. 8 is a block diagram illustrating a configuration of an image display device according to a second embodiment of the invention.

Next, an image display device according to a second embodiment of the invention will be described. FIG. 8 is a block diagram illustrating a configuration of the image display device according to the second embodiment. An image display device 5-2 illustrated in FIG. 8 includes a preferential image determination unit 63 provided in the subsequent stage of the display image processing unit 53; and a preferential process control unit 64 controlling the position information acquisition unit 57. Other configurations thereof are the same as those illustrated in FIG. 4.

In the second embodiment, during examination by the capsule endoscope 2 (that is, while the capsule endoscope 2 moves through the subject 10), a user (a person in charge of the examination such as a doctor or the like) observes internal body images in real time, and marks desired internal body images. Specifically, the internal body images are displayed on the display unit 36 of the receiver 3 illustrated in FIG. 3, so that the user observes the internal body images and inputs marking information to the receiver when he/she recognizes a boundary between organs such as the stomach, the small intestine, and the large intestine, or recognizes a site of lesion. The marking information is taken into the image display device 5 as related information of the internal body image data. Alternatively, a separate viewer may be connected to the receiver 3 to display the internal body images on the viewer for the user's observation, instead of the display unit 36.

The preferential image determination unit 63 determines whether the marking information is included in the related information of the internal body image data subjected to the display image processing, and provides a flag indicative of preferential images to the internal body image data including the marking information.

The preferential process control unit 64 controls the position information acquisition unit 57 to perform preferentially the position estimation process on the internal body image data provided with the flag by the preferential image determination unit 63.

Figure 9:
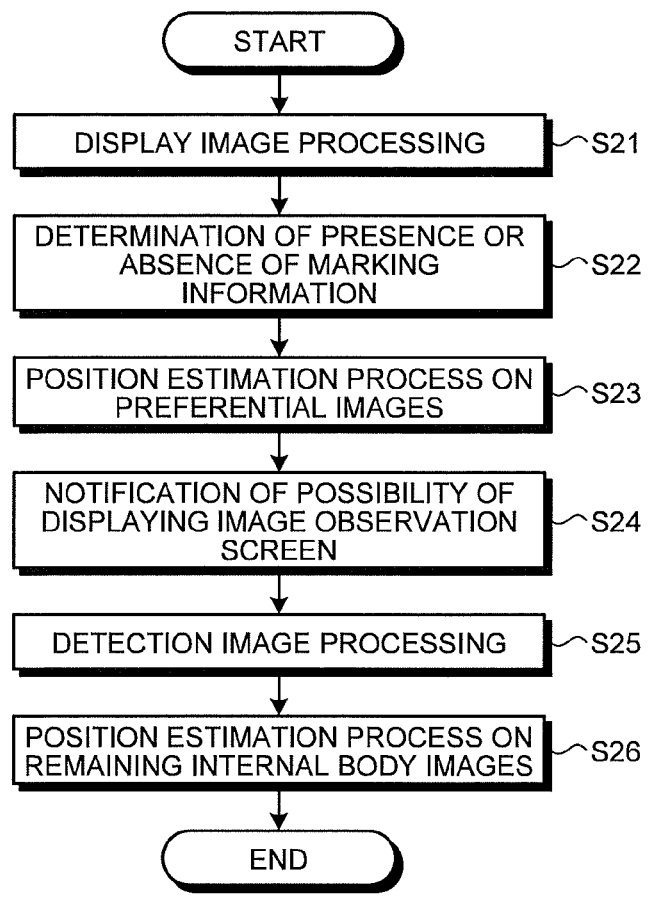
FIG. 9 is a flowchart showing an operation of the image display device illustrated in FIG. 8.

Next, referring to FIG. 9, an operation of the image display device 5-2 will be described. FIG. 9 is a flowchart showing an operation of the image display device 5-2.

At step S21, the display image processing unit 53 performs the display image processing on the internal body image data stored in the temporary memory unit 52. At subsequent step S22, the preferential image determination unit 63 provides a flag indicative of preferential images to the internal body image data having the marking information. The internal body image data subjected to the display image processing is stored in the memory unit 55.

At step S23, the position information acquisition unit 57 retrieves sequentially related information of the internal body image data provided with the flag indicative of preferential images, from the memory unit 55, and performs the position estimation process on the related information, under control of the preferential process control unit 64. Resultant position information is stored in the memory unit 55 in association with the internal body image data.

At the image display device 5-2, when the position estimation process on the preferential images is completed, the internal body images and the required position information can be displayed on the display unit 59. Accordingly, at step S24, the display control unit 58 causes the display unit 59 to display a message informing that the radiogram interpretation screen can be displayed. After display of the message, the display control unit 58 may cause the display unit 59 to display the radiogram interpretation screen (see FIGS. 6 and 7) after lapse of a predetermined period of time, or may cause the display unit 59 to display a screen allowing the user to select whether to actually display the radiogram interpretation screen with the message. In the latter case, the display control unit 58 causes the display unit 59 to display the radiogram interpretation screen when a signal to select the display of the radiogram interpretation screen by the user's operation. In addition, minified images of the preferential images may be displayed in the thumbnail area 116 of the radiogram interpretation screen.

At step S25, the detection image processing unit 56 retrieves sequentially the internal body image data stored in the memory unit 55, and performs the detection image processing on the retrieved data. At subsequent step S26, the position information acquisition unit 57 retrieves sequentially related information of the internal body image data other than the preferential images from the memory unit 55, and performs the position estimation process on the retrieved information. If the radiogram interpretation screen is displayed on the display unit 59, the display control unit 58 controls the display unit 59 to display in sequence the additional points 121 indicative of the imaging positions of the internal body images subjected to the position estimation process, in the position display area 118. At that time, the points 121 corresponding to the preferential images and the points 121 corresponding to the internal body images other than the preferential images may be displayed by different colors, marks, or brightnesses, for example, so that these points 121 can be differentiated.

Upon completion of the position estimation process on all of the internal body images, the data process by the image display device 5-2 is terminated. After that, if display of the radiogram interpretation screen has already started, the image display device 5-2 continues to display the radiogram interpretation screen. In contrast, if display of the radiogram interpretation screen is not started after step S24, the image display device 5-2 may display a new screen that allows the user to select whether to start display of the radiogram interpretation screen.

As described above, according to the second embodiment, the position estimation process is preferentially performed on the internal body images (marked internal body images) attracting the user's attention during the examination, and therefore, the user can early grasp the imaging positions of the internal body images determined as important by himself/herself, and can efficiently perform interpretation of radiogram.

In the foregoing description, after completion of the display image processing on all of the internal body image data, the position information acquisition unit 57 starts the position estimation process on the preferential images. Alternatively, the position information acquisition unit 57 may retrieve related information directly from the temporary memory unit 52 and perform the position estimation process in parallel with the display image processing. In this case, the preferential process control unit 64 controls the position information acquisition unit 57 to, at generation of any preferential image, interpose the preferential image to the display image processing and perform the position estimation process on the preferential image.

Third Embodiment

Figure 10:
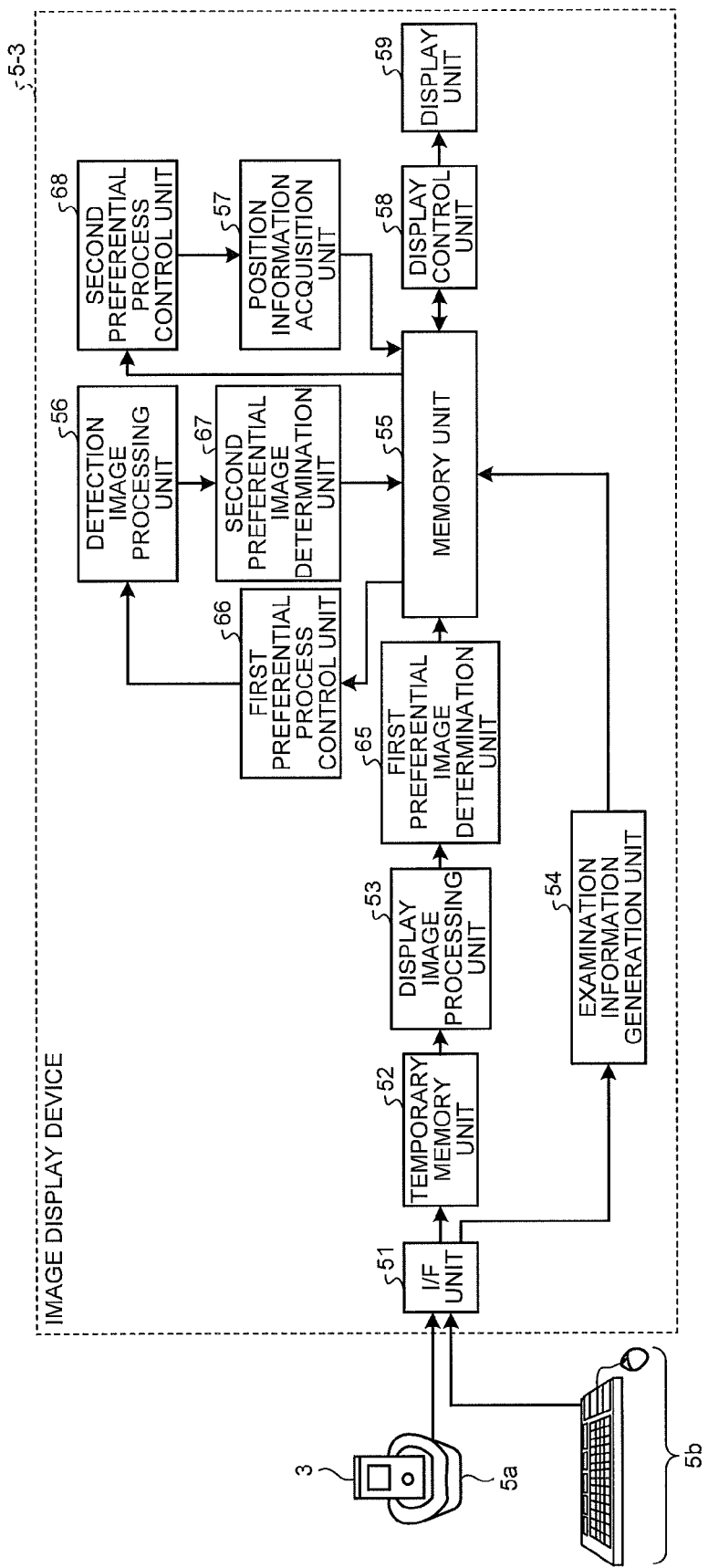
FIG. 10 is a block diagram illustrating a configuration of an image display device according to a third embodiment of the invention.

Next, an image display device according to a third embodiment of the invention will be described. FIG. 10 is a block diagram illustrating a configuration of the image display device according to the third embodiment. An image display device 5-3 illustrated in FIG. 10 includes: a first preferential image determination unit 65; a first preferential process control unit 66; a second preferential image determination unit 67; and a second preferential process control unit 68. Other configurations thereof are the same as those illustrated in FIG. 4. In the third embodiment, a user observes internal body images in real time and marks desired internal body images during examination by the capsule endoscope 2, as in the second embodiment.

The first preferential image determination unit 65 determines whether marking information is included in the related information of the internal body image data subjected to the display image processing, and provides a flag indicative of preferential images to the internal body image data including the marking information.

The first preferential process control unit 66 controls the detection image processing unit 56 to perform preferentially the detection image processing on the internal body image data provided with the flag by the preferential image determination unit 65.

The second preferential image determination unit 67 determines whether a site of lesion or a boundary between organs is extracted from the internal body images subjected to the detection image processing, and provides a flag indicative of preferential images to the internal body image data from which a site of lesion or a boundary between organs is extracted.

The second preferential process control unit 68 controls the position information acquisition unit 57 to perform preferentially the position estimation process on the internal body image data provided with the flag by the second preferential image determination unit 67.

Figure 11:
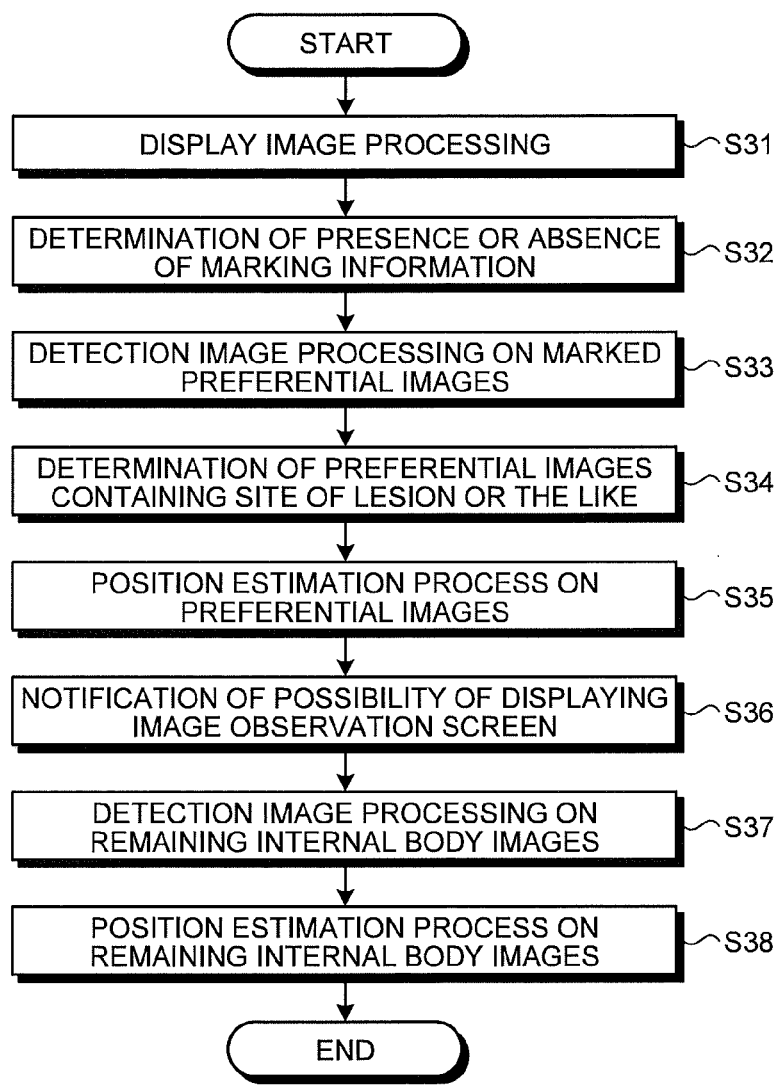
FIG. 11 is a flowchart showing an operation of the image display device illustrated in FIG. 10.

Next, an operation of the image display device 5-3 will be described with reference to FIG. 11. FIG. 11 is a flowchart showing the operation of the image display device 5-3.

At step S31, the display image processing unit 53 performs the display image processing on the internal body image data stored in the temporary memory unit 52.

At subsequent step S32, the first preferential image determination unit 65 provides a flag indicative of marked preferential images to the internal body image data having the marking information. The internal body image data subjected to the display image processing is stored in the memory unit 55.

At step S33, the detection image processing unit 56 retrieves sequentially the internal body image data provided with the flag indicative of the marked preferential images, from the memory unit 55, and performs the detection image processing on the retrieved data, under control of the first preferential process control unit 66.

At step S34, the second preferential image determination unit 67 provides a flag indicative of preferential images including a site of lesion or the like to the internal body image data in which a site of lesion or a boundary between organs is detected by the detection image processing unit 56.

At step S35, the position information acquisition unit 57 retrieves sequentially related information of the internal body image data provided with the flag indicative of preferential images including a site of lesion or the like, and performs the position estimation process on the retrieved information, under control of the second preferential process control unit 68. That is, at step S35, the position information acquisition unit 57 performs the position estimation process on the internal body images having the marking information and in which a site of lesion or the like is detected.

At the image display device 5-3, when the position estimation process on the marked preferential images including a site of lesion or the like is completed, the internal body images and the necessary position information can be displayed on the display unit 59. Accordingly, upon completion of the position estimation process at step S35, the display control unit 58 causes the display unit 59 to display a message informing that the radiogram interpretation screen can be displayed at step S36. After display of the message, the display control unit 58 may cause the display unit 59 to display the radiogram interpretation screen (see FIGS. 6 and 7) after lapse of a predetermined period of time, or may cause the display unit 59 to display a screen allowing the user to select whether to display the radiogram interpretation screen with the message. In the latter case, the display control unit 58 causes the display unit 59 to display the radiogram interpretation screen when a signal to select the display of the radiogram interpretation screen by the user's operation.

At step S37, the detection image processing unit 56 retrieves sequentially the internal body image data of the preferential images other than the marked preferential images from the memory unit 55, and performs the detection image processing on the retrieved data. At subsequent step S38, the position information acquisition unit 57 retrieves sequentially related information of the internal body image data other than the preferential images including a site of lesion or the like from the memory unit 55, and performs the position estimation process on the retrieved information. If the radiogram interpretation screen is displayed on the display unit 59, the display control unit 58 controls the display unit 59 to display in sequence the additional points 121 indicative of the imaging positions of the internal body images subjected to the position estimation process, in the position display area 118. At that time, the points 121 corresponding to the preferential images and the points 121 corresponding to the internal body images other than the preferential images may be displayed by different colors, marks, or brightnesses, for example, so that these points 121 can be differentiated.

Upon completion of the detection image processing and the position estimation process on all of the internal body images, the data process by the image display device 5-3 is terminated. After that, if display of the radiogram interpretation screen has already started, the image display device 5-3 continues to display the radiogram interpretation screen. In contrast, if display of the radiogram interpretation screen is not started after step S36, the image display device 5-3 may display a new screen that allows the user to select whether to start display of the radiogram interpretation screen.

As described above, according to the third embodiment, the detection image processing is performed on the internal body images (marked internal body images) attracting the user's attention during the examination, and as a result, the position estimation process is preferentially performed on the internal body images in which a site of lesion or the like is detected. Accordingly, the user can early grasp the imaging positions of the internal body images determined as important by himself/herself and determined to be noted by the image processing, and can efficiently perform interpretation of radiogram.

In the foregoing description, after completion of the display image processing on all of the internal body image data, the detection image processing unit 56 starts the detection image processing on the preferential images. Alternatively, when the internal body image data subjected to the display image processing starts to be stored in the memory unit 55, the detection image processing unit 56 may perform the detection image processing in parallel with the display image processing. In this case, the first preferential process control unit 66 controls the detection image processing unit 56 to, at generation of any preferential image, interpose the preferential image to the display image processing and perform the detection image processing on the preferential image.

In the foregoing description, after completion of the detection image processing on the marked preferential images, the position information acquisition unit 57 starts the position estimation process on the preferential images including a site of lesion or the like. Alternatively, the position information acquisition unit 57 may retrieve related information directly from the temporary memory unit 52 and perform the position estimation process in parallel with the display image processing and the detection image processing. In this case, the second preferential process control unit 68 controls the position information acquisition unit 57 to, at generation of any preferential image including a site of lesion or the like, interpose the preferential image to the display image processing and perform the position estimation process on the preferential image.

Fourth Embodiment

Figure 12:
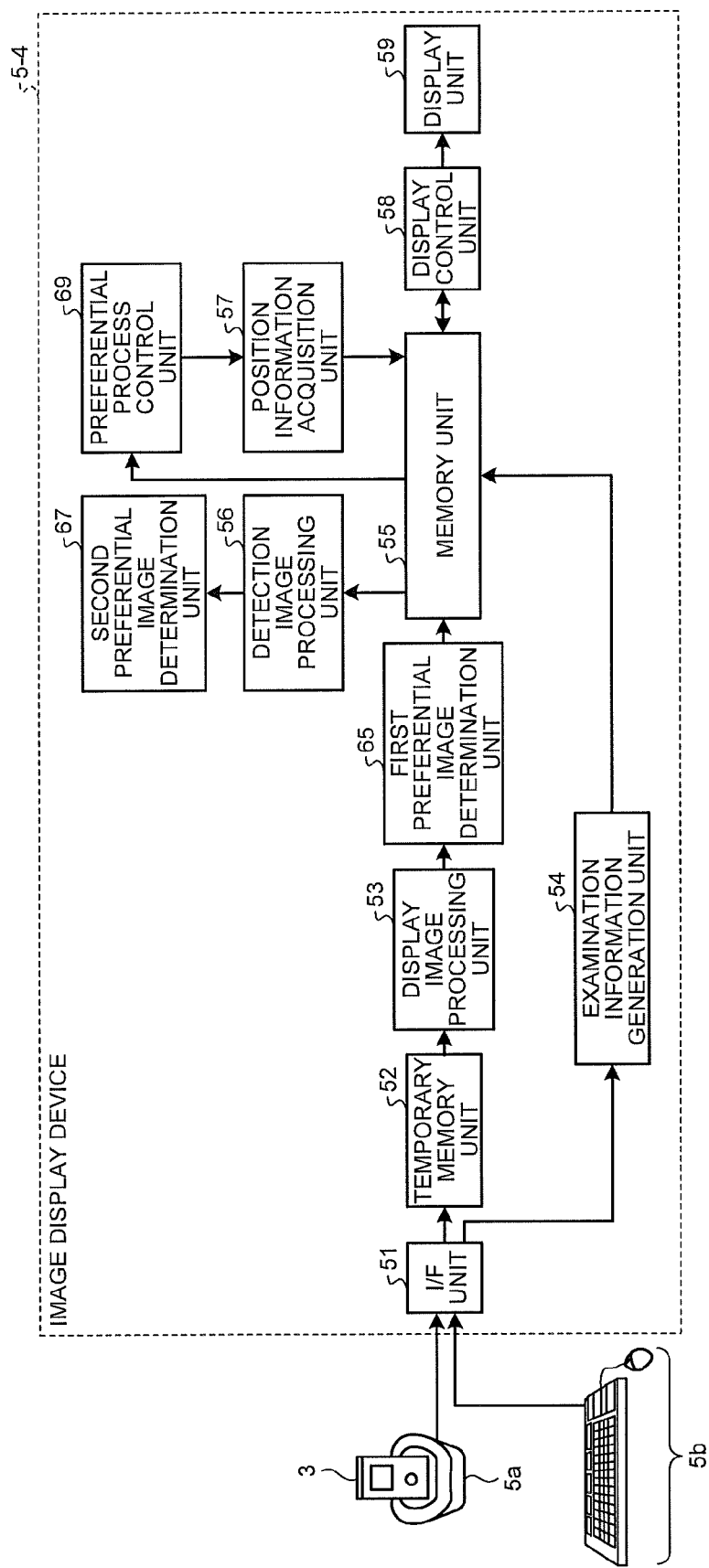
FIG. 12 is a block diagram illustrating a configuration of an image display device according to a fourth embodiment of the invention.

Next, an image display device according to a fourth embodiment of the invention will be described. FIG. 12 is a block diagram illustrating a configuration of the image display device according to the fourth embodiment. An image display device 5-4 illustrated in FIG. 12 includes a first preferential image determination unit 65, a second preferential image determination unit 67, and a preferential process control unit 69. Operations of the first preferential image determination unit 65 and the second preferential image determination unit 67 are the same as those described above in relation to the third embodiment. Other configurations of the fourth embodiment are the same as those illustrated in FIG. 4. In the fourth embodiment, a user observes internal body images in real time and marks desired internal body images during examination by the capsule endoscope 2, as in the second embodiment.

The preferential process control unit 69 controls the position information acquisition unit 57 to perform preferentially the position estimation process on the internal body image data provided with the flag by the first preferential image determination unit 65 (that is, the marked preferential images) and on the internal body image data provided with the flag by the second preferential image determination unit 67 (that is, the preferential images including a site of lesion or the like).

Figure 13:
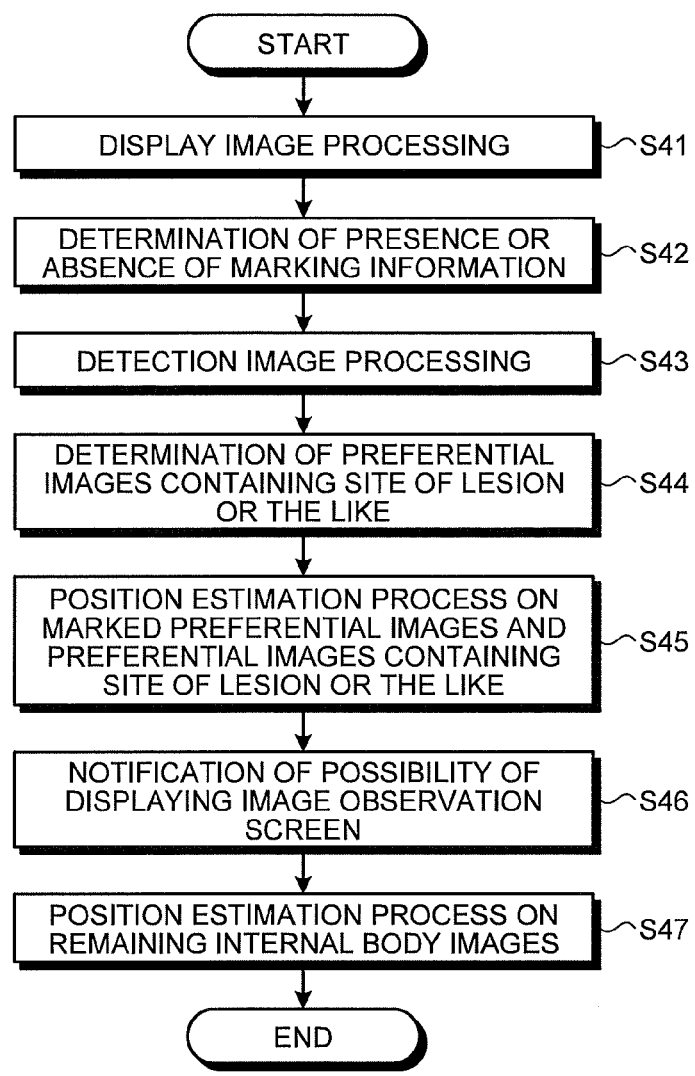
FIG. 13 is a flowchart showing an operation of the image display device illustrated in FIG. 12.

Next, an operation of the image display device 5-4 will be described with reference to FIG. 13. FIG. 13 is a flowchart showing the operation of the image display device 5-4.

At step S41, the display image processing unit 53 performs the display image processing on the internal body image data stored in the temporary memory unit 52.

At subsequent step S42, the first preferential image determination unit 65 provides a flag indicative of marked preferential images to the internal body image data having the marking information. The internal body image data subjected to the display image processing is stored in the memory unit 55.

At step S43, the detection image processing unit 56 retrieves sequentially the internal body image data stored in the memory unit 55 and performs the detection image processing on the retrieved internal body image data.

At subsequent step S44, the second preferential image determination unit 67 provides a flag indicative of preferential images including a site of lesion or the like to the internal body image data in which a site of lesion or a boundary between organs or the like is detected by the detection image processing unit 56.

At step S45, the position information acquisition unit 57 retrieves sequentially from the memory unit 55 related information of the internal body image data provided with the flag indicative of marked preferential images and related information of the internal body image data provided with the flag indicative of preferential images including a site of lesion or the like, and performs the position estimation process on the retrieved information, under control of the preferential process control unit 69. That is, at step S45, the position information acquisition unit 57 performs the position estimation process on the internal body images having the marking information or in which a site of lesion or the like is detected.

At the image display device 5-4, when the position estimation process on the marked preferential images or the preferential images including a site of lesion or the like is completed, the internal body images and the necessary position information can be displayed on the display unit 59. Accordingly, upon completion of the position estimation process at step S45, the display control unit 58 causes the display unit 59 to display a message informing that the radiogram interpretation screen can be displayed at step S46. After display of the message, the display control unit 58 may cause the display unit 59 to display the radiogram interpretation screen (see FIGS. 6 and 7) after lapse of a predetermined period of time, or may cause the display unit 59 to display a screen allowing the user to select whether to actually display the radiogram interpretation screen. In the latter case, the display control unit 58 causes the display unit 59 to display the radiogram interpretation screen when a signal to select the display of the radiogram interpretation screen by the user's operation.

At step S47, the position information acquisition unit 57 retrieves sequentially related information of the internal body image data other than the marked preferential images or the preferential images including a site of lesion or the like from the memory unit 55, and performs the position estimation process on the retrieved information. If the radiogram interpretation screen is displayed on the display unit 59, the display control unit 58 may control the display unit 59 to display in sequence the additional points 121 indicative of the imaging positions of the internal body images subjected to the position estimation process, in the position display area 118. At that time, the points 121 corresponding to the marked preferential images, the points 121 corresponding to the preferential images including a site of lesion or the like, and the points 121 corresponding to the internal body images other than the preferential images, may be displayed by different colors, marks, or brightnesses, for example, so that these points 121 can be differentiated.

Upon completion of the position estimation process on all of the internal body images, the data process by the image display device 5-4 is terminated. After that, if display of the radiogram interpretation screen has already started, the image display device 5-4 continues to display the radiogram interpretation screen. In contrast, if display of the radiogram interpretation screen is not started after step S46, the image display device 5-4 may display a new screen that allows the user to select whether to start display of the radiogram interpretation screen.

As described above, according to the fourth embodiment, the position estimation process is preferentially performed on both the internal body images attracting the user's attention during the examination and the internal body images in which a site of lesion or the like is detected. Accordingly, the user can widely and early grasp the imaging positions of the internal body images determined as important by himself/herself and determined to be noted by the image processing, and can efficiently perform interpretation of radiogram.

In the foregoing description, after completion of the display image processing on all of the internal body image data, the detection image processing unit 56 starts the detection image processing. Alternatively, when the internal body image data subjected to the display image processing starts to be stored in the memory unit 55, the detection image processing unit 56 may perform the detection image processing in parallel with the display image processing.

In the foregoing description, after completion of the detection image processing on all of the internal body image data, the position information acquisition unit 57 starts the position estimation process on the preferential images. Alternatively, the position information acquisition unit 57 may perform the position estimation process in parallel with the detection image processing. Alternatively, the position information acquisition unit 57 may retrieve related information directly from the temporary memory unit 52 and perform the position estimation process in parallel with the display image processing and the detection image processing. In these cases, the preferential process control unit 69 controls the position information acquisition unit 57 to, at generation of any preferential image determined by the first preferential image determination unit 65 or the second preferential image determination unit 67, interpose the preferential image to the display image processing and the detection image processing and perform the position estimation process on the preferential image.

Fifth Embodiment

Figure 14:
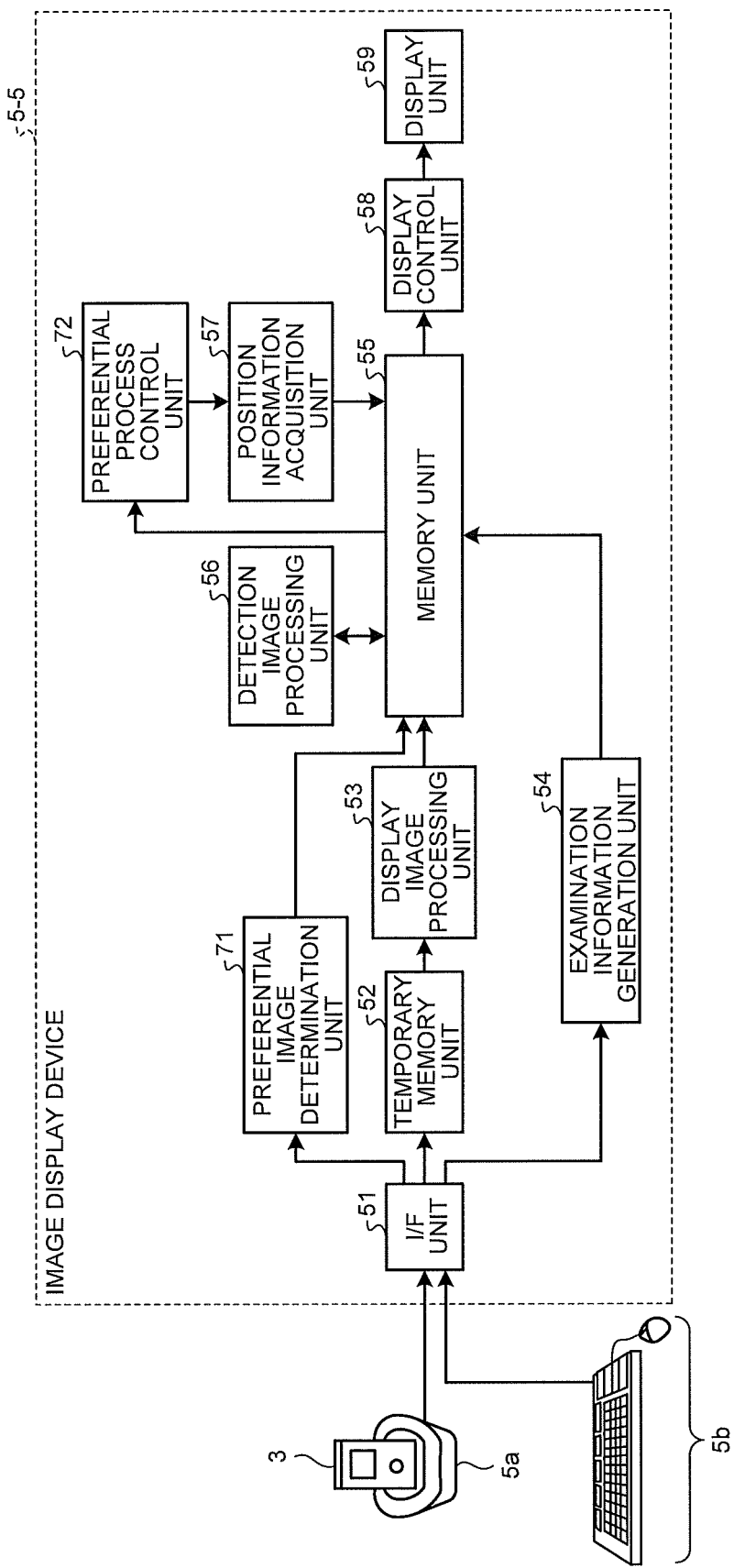
FIG. 14 is a block diagram illustrating a configuration of an image display device according to a fifth embodiment of the invention.

Next, an image display device according to a fifth embodiment of the invention will be described. FIG. 14 is a block unit illustrating a configuration of the image display device according to the fifth embodiment. An image display device 5-5 illustrated in FIG. 14 includes a preferential image determination unit 71 and a preferential process control unit 72. Other configurations thereof are the same as those illustrated in FIG. 4. The image display device 5-5 is characterized by allowing a user to select desired internal body images as preferential images using the operation input device 5b while observing the radiogram interpretation screen displayed on the display unit 59.

The preferential image determination unit 71 determines whether the position estimation process on the internal body images selected by the user is completed based on an operation signal externally input via the interface unit 51. If the position estimation process is not completed, the preferential image determination unit 71 provides a flag indicative of preferential images to the selected internal body image data.

The preferential process control unit 72 controls the position information acquisition unit 57 to perform the position estimation process preferentially on the internal body image data provided with the flag by the preferential image determination unit 71.

Figure 15:
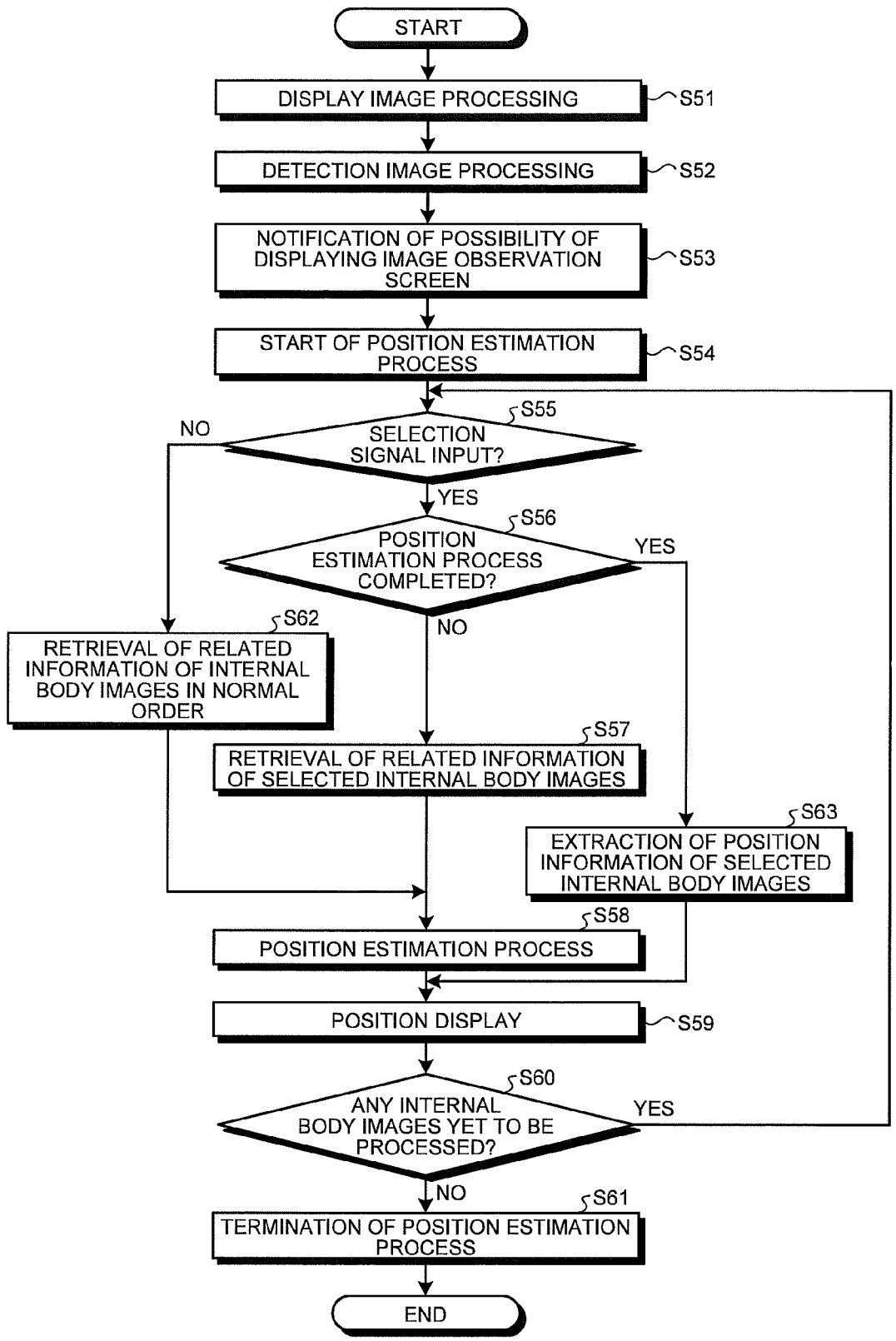
FIG. 15 is a flowchart showing an operation of the image display device illustrated in FIG. 14.

Next, an operation of the image display device 5-5 will be described with reference to FIGS. 15 to 17. FIG. 15 is a flowchart showing an operation of the image display device 5-5.

At step S51, the display image processing unit 53 performs the display image processing on the internal body image data stored in the temporary memory unit 52. The internal body image data subjected to the display image processing is stored in the memory unit 55. At subsequent step S52, the detection image processing unit 56 retrieves sequentially the internal body image data subjected to the display image processing from the memory unit 55, and performs the detection image processing on the retrieved data.

At the image display device 5-5, when the detection image processing is completed, the internal body images can be displayed on the display unit 59. Accordingly, upon completion of the detection image processing at step S52, the display control unit 58 causes the display unit 59 to display a message informing that the radiogram interpretation screen can be displayed at step S53. After display of the message, the display control unit 58 may cause the display unit 59 to display the radiogram interpretation screen after lapse of a predetermined period of time, or may cause the display unit 59 to display a screen allowing the user to select whether to actually display the radiogram interpretation screen with the message. In the latter case, the display control unit 58 causes the display unit 59 to display the radiogram interpretation screen when a signal to select display of the radiogram interpretation screen by the user's operation.

Figure 16:
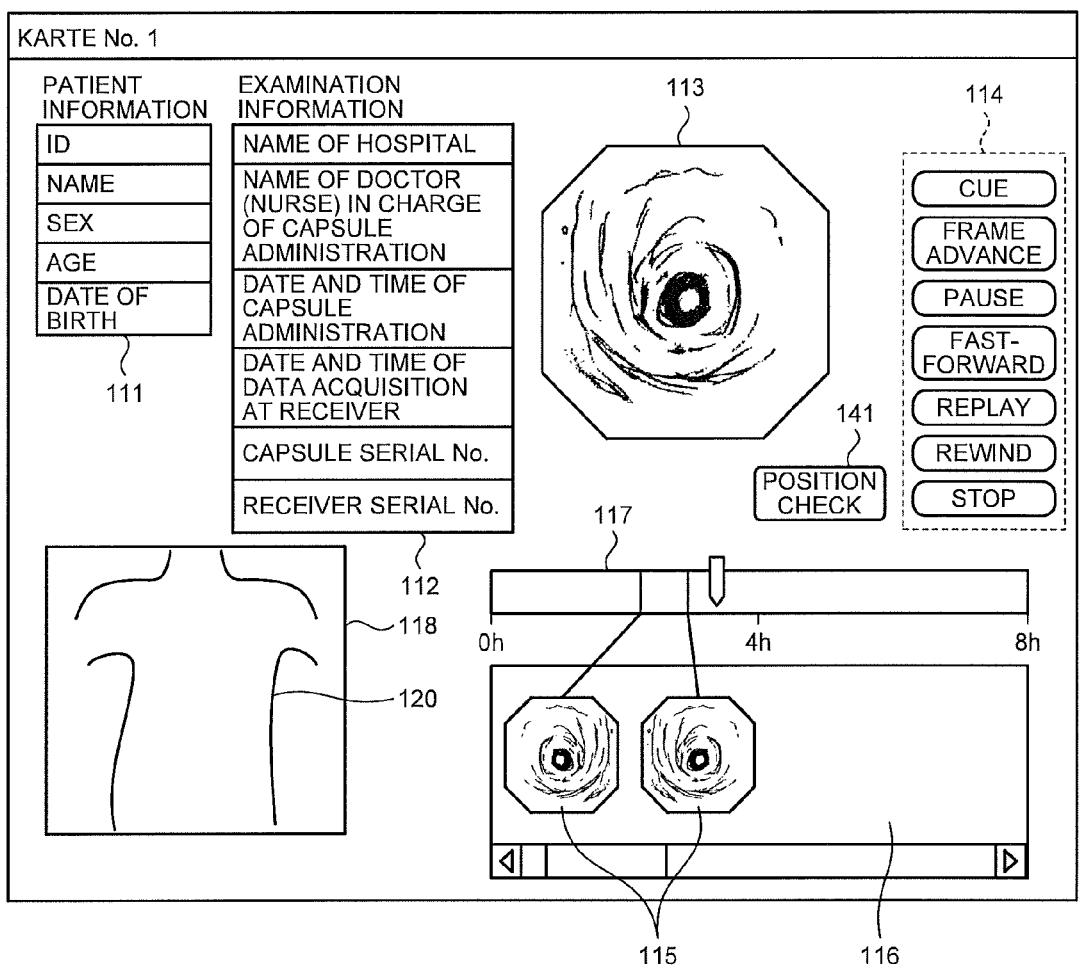
FIG. 16 is a block diagram illustrating a display example of a radiogram interpretation screen displayed on the image display device illustrated in FIG. 14.

FIG. 16 is a schematic diagram illustrating a display example of the radiogram interpretation screen that can be displayed after step S53. A radiogram interpretation screen 140 includes a button 141 that is clicked by the user if he/she wishes to display the imaging positions of the internal body images currently displayed in the main display area 113.

At subsequently step S54, the image display device 5-5 starts the position estimation process.

First, at step S55, the image display device 5-5 determines whether a selection signal to select internal body images currently displayed is input by the user's operation using the operation input device 5b (for example, clicking on the "position check" button 141).

If the selection signal is input (step S55: Yes), the preferential image determination unit 71 determines whether the position estimation process has already performed on the selected internal body images (step S56). If the position estimation process has not yet performed (step S56: No), the preferential image determination unit 71 provides a flag indicative of preferential images to the selected internal body image data. In response to this, at step S57, the position information acquisition unit 57 retrieves related information of the internal body image data provided with the flag, from the memory unit 55 under control of the preferential process control unit 72.

At step S58, the position information acquisition unit 57 performs the position estimation process based on the retrieved related information. At subsequent step S59, the display control unit 58 causes the display unit 59 to display the imaging positions of the internal body images on the radiogram interpretation screen, based on the resultant position information generated by the position estimation process.

After that, if there exists any internal body image not subjected to the position estimation process (step S60: Yes), the process returns to step S55. In contrast, if the position estimation process is performed on all of the internal body images (step S60: No), the position estimation process is terminated (step S61).

Figure 17:
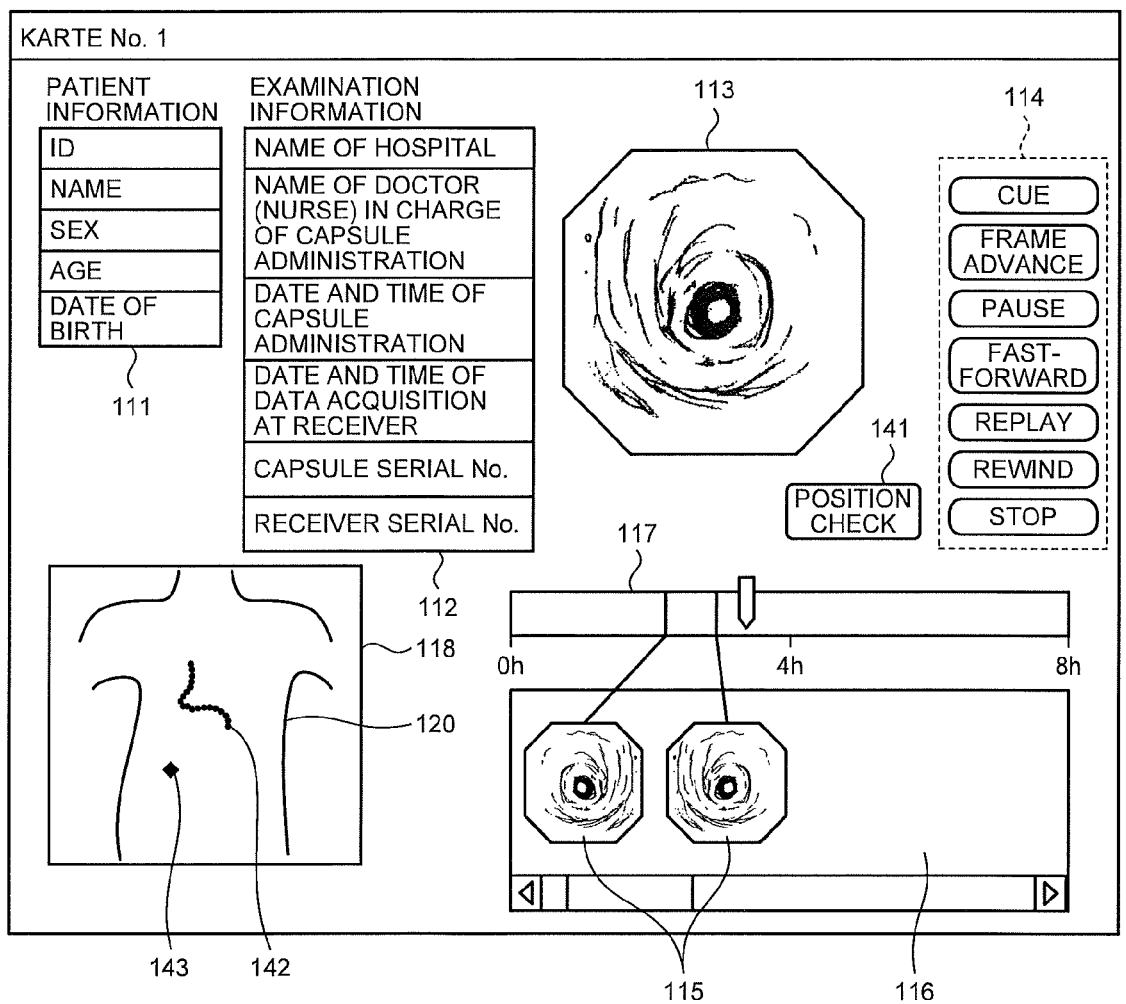
FIG. 17 is a block diagram illustrating a display example of a radiogram interpretation screen displayed on the image display device illustrated in FIG. 14.

FIG. 17 is a schematic diagram illustrating a display example of imaging positions of internal body images on the radiogram interpretation screen 140. The imaging positions of the internal body images subjected to the position estimation process so far are indicated by points 142 on the personal image 120 displayed in the position display area 118. In addition, the imaging positions of the selected internal body images are indicated by points 143. The points 143 may be provided by a color, brightness, or mark different from that of the points 142, so that the points 143 can be differentiated from the points 142.

In contrast, if no selection signal is input (step S55: No), the position information acquisition unit 57 retrieves related information of the internal body image data in normal order (for example, order of transfer of internal body image data) (step S62). After that, the process moves to step S58.

In addition, if the selection signal is input (step S55: Yes) but the position estimation process has already performed on the selected internal body images (step S56: Yes), the display control unit 58 extracts position information of the selected internal body images from the memory unit 55 (step S63). After that, the process moves to step S59.

As described above, according to the fifth embodiment, the position estimation process is preferentially performed on the internal body images selected by the user performing the radiogram interpretation. Therefore, the user can grasp early the imaging positions of the internal body images determined as needed during the radiogram interpretation.

The preferential image determination unit 71 and the preferential process control unit 72 in the fifth embodiment can be provided to the image display devices according to the first to fourth embodiments. In this case, the position information acquisition unit 57 may perform the position estimation process preferentially on internal body images selected by the user during radiogram interpretation, than marked preferential images and preferential images including a site of lesion or the like.

Sixth Embodiment

Figure 18:
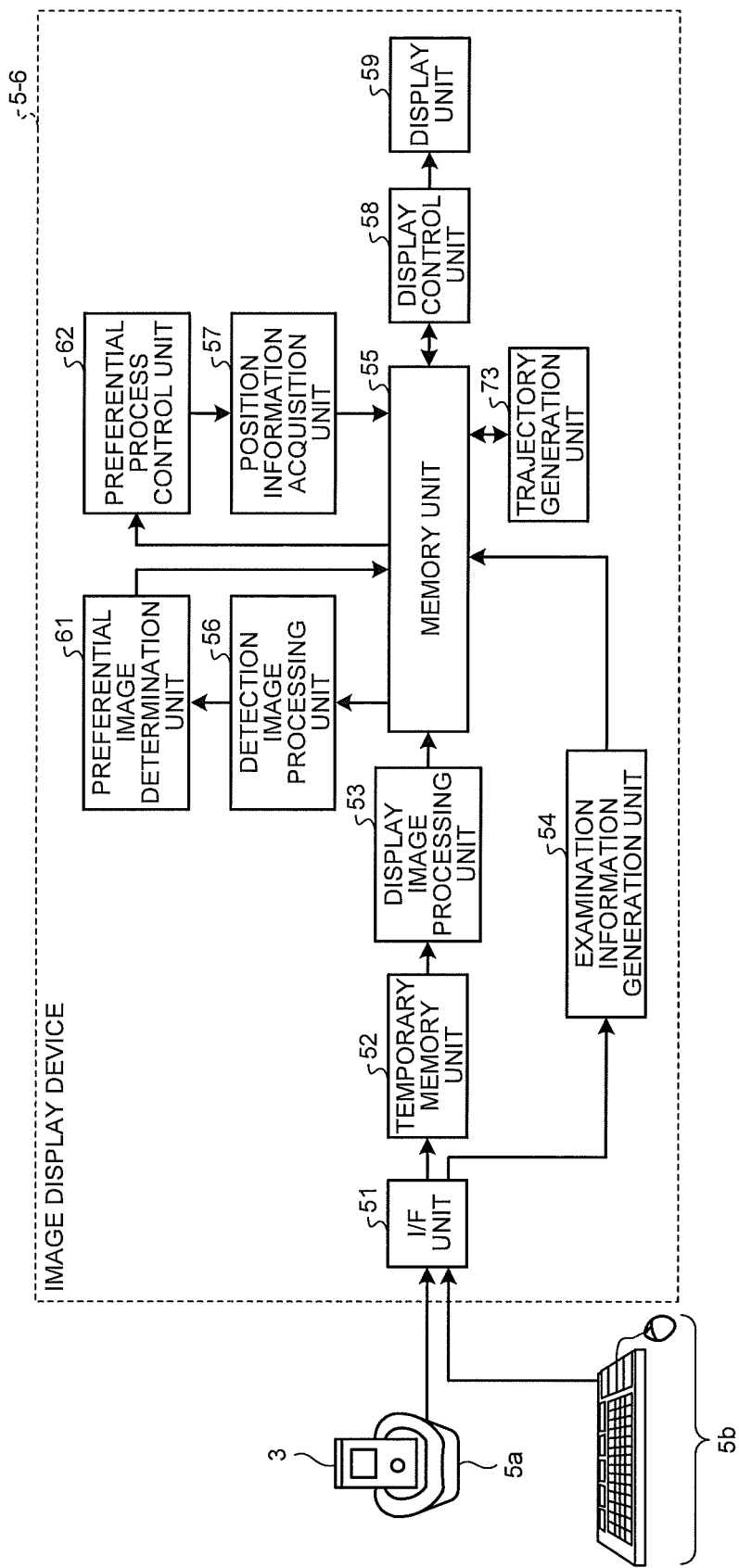
FIG. 18 is a block diagram illustrating a configuration of an image display device according to a sixth embodiment of the invention.

Next, an image display device according to a sixth embodiment of the invention will be described. FIG. 18 is a block diagram illustrating a configuration of the image display device according to the sixth embodiment. An image display device 5-6 illustrated in FIG. 18 includes a trajectory generation unit 73. Other configurations thereof are the same as those illustrated in FIG. 4.

After the position estimation process is performed all of the internal body images, the trajectory generation unit 73 performs a trajectory generation process to generate a path trajectory of the capsule endoscope 2 from introduction into the subject 10 to ejection from the subject 10. Specifically, the trajectory generation unit 73 extracts two temporally adjacent points from a plurality of positions of the capsule endoscope 2 at imaging of the internal body images, based on position information generated by the position information acquisition unit 57, and then connects these two points to each other. The trajectory generation unit 73 connects the thus estimated positions in sequence, thereby generating a total trajectory. Information indicative of the generated trajectory (trajectory information) is stored in the memory unit 55. Various known methods may be applied to the specific method of the trajectory generation process besides the foregoing one.

Figure 19:
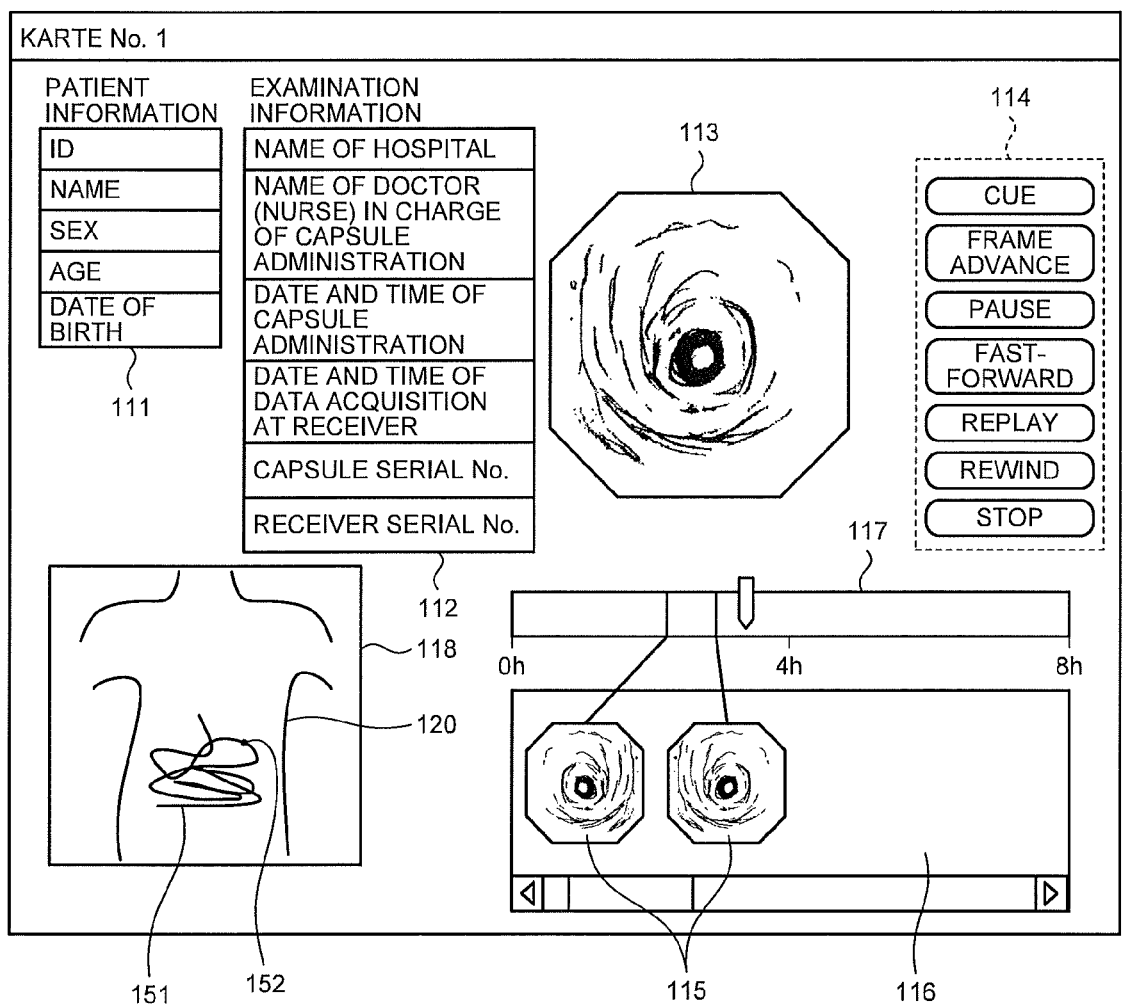
FIG. 19 is a schematic diagram illustrating a display example of a radiogram interpretation screen displayed on the image display device illustrated in FIG. 18.

FIG. 19 is a schematic diagram illustrating a display example of a trajectory on the radiogram interpretation screen. A trajectory 151 drawn based on the trajectory information is displayed on the personal image 120 displayed in the position display area 118 of a radiogram interpretation screen 150. At that time, in the position display area 118, a point 152 indicative of the imaging position of the internal body image currently displayed in the main display area 113, is shown on the trajectory 151.

As described above, according to the sixth embodiment, a trajectory of the capsule endoscope 2 is displayed on the radiogram interpretation screen, and therefore the user can grasp more accurately the positions of internal body images of the subject 10 under radiogram interpretation.

The trajectory generation unit 73 in the sixth embodiment may be provided to the image display devices according to the second to fifth embodiments.

As described above, according to the first to sixth embodiments, the position estimation process is preferentially performed on internal body images meeting a predetermined condition, which makes it possible to acquire more early position information of the internal body images needed for performing a diagnosis. Therefore, the radiogram interpretation screen can be displayed early based on internal body image data subjected to the display image processing and preferentially acquired position information.

The first to sixth embodiments described above are merely examples for carrying out the invention. However, the invention is not limited to the embodiments but may be modified in various manners according to the specification within the scope of the invention. In addition, it is obvious from the foregoing description that other various embodiments can be possible within the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display device that displays an internal body image group based on internal body image data acquired from a capsule endoscope taking internal body images of a subject, the image display device comprising:
    a memory unit that stores the internal body image data and information associated with the internal body image data and related to a position of the capsule endoscope within the subject;
    a position information acquisition unit that performs a position estimation process based on the information related to a position to acquire position information of the capsule endoscope at imaging of each of the internal body images;
    a determination unit that determines whether results of predetermined image processing on the internal body image data meet a condition for performing a preferential process and provides a flag to the internal body image data meeting the condition;
    a preferential process control unit that controls the position information acquisition unit to perform the position estimation process on the internal body image data provided with the flag by the determination unit;
    a display image processing unit that performs display image processing on the internal body image data stored in the memory unit;
    a display unit that displays an image observation screen having an image display area in which a plurality of internal body images constituting the internal body image group is sequentially displayed based on the internal body image data subjected to the display image processing and a position information display area in which position information acquired by the position information acquisition unit is displayed; and
    a display control unit that causes the display unit to display the image observation screen after completion of the position estimation process performed under control of the preferential process control unit, wherein,
    after performing the position estimation process on the internal body image data provided with the flag, the position information acquisition unit performs the position estimation process on remaining internal body image data other than the internal body image data provided with the flag,
    the display control unit causes the display unit to display results of the position estimation process on the remaining internal body image data in the position information display area, and
    the display control unit causes the display unit to display results of the position estimation process on the internal body image data provided with the flag and results of the position estimation process on the remaining internal body image data, in a distinguishable display forms in the position information display area.

2. The image display device according to claim 1, further comprising an input signal reception unit that receives a signal input from outside to the image display device, wherein
    if the input signal reception unit receives a selection signal indicative of selection of a predetermined internal body image, the preferential process control unit causes the position estimation process to be preferentially performed on the predetermined internal body image.

3. A capsule endoscope system, comprising:
- a capsule endoscope that is introduced in a body of a subject to take images and generate internal body image data representing internal body images of the subject;
- a receiver that receives the internal body image data generated by the capsule endoscope via wireless communication; and
- the image display device according to claim 1.

4. The image display device according to claim 1, wherein, after completion of the position estimation process performed under control of the preferential process control unit, the display control unit displays a message informing that the image observation screen can be displayed on the display unit.

5. An image display device that displays an internal body image group based on internal body image data acquired from a capsule endoscope taking internal body images of a subject, the image display device comprising:
- a memory unit that stores the internal body image data and information associated with the internal body image data and related to a position of the capsule endoscope within the subject;
- a position information acquisition unit that performs a position estimation process based on the information related to a position to acquire position information of the capsule endoscope at imaging of each of the internal body images;
- a determination unit that determines whether results of predetermined image processing on the internal body image data meet a condition for performing a preferential process and provides a flag to the internal body image data meeting the condition;
- a preferential process control unit that controls the position information acquisition unit to perform the position estimation process on the internal body image data provided with the flag by the determination unit;
- a display image processing unit that performs display image processing on the internal body image data stored in the memory unit;
- a display unit that displays an image observation screen having an image display area in which a plurality of internal body images constituting the internal body image group is sequentially displayed based on the internal body image data subjected to the display image processing and a position information display area in which position information acquired by the position information acquisition unit is displayed; and
- a display control unit that causes the display unit to display the image observation screen after completion of the position estimation process performed under control of the preferential process control unit, wherein,
- after performing the position estimation process on the internal body image data provided with the flag, the position information acquisition unit performs the position estimation process on remaining internal body image data other than the internal body image data provided with the flag,
- the position information display area has a plurality of divided areas divided in a matrix, and the divided areas corresponding to the position information are displayed in a predetermined color or pattern, and
- after completion of the position estimation process performed under control of the preferential process control unit, the display control unit sub-divides the divided areas according to progress of the position estimation process on the remaining internal body image data, and causes the display unit to display the sub-divided areas.

6. The image display device according to claim 5, further comprising an input signal reception unit that receives a signal input from outside to the image display device, wherein
- if the input signal reception unit receives a selection signal indicative of selection of a predetermined internal body image, the preferential process control unit causes the position estimation process to be preferentially performed on the predetermined internal body image.

7. A capsule endoscope system, comprising:
- a capsule endoscope that is introduced in a body of a subject to take images and generate internal body image data representing internal body images of the subject;
- a receiver that receives the internal body image data generated by the capsule endoscope via wireless communication; and
- the image display device according to claim 5.

8. The image display device according to claim 5, wherein, after completion of the position estimation process performed under control of the preferential process control unit, the display control unit displays a message informing that the image observation screen can be displayed on the display unit.

* * * * *